(12) United States Patent
Osorio

(10) Patent No.: US 11,000,685 B2
(45) Date of Patent: May 11, 2021

(54) SYSTEM AND APPARATUS FOR AUTOMATED QUANTITATIVE ASSESSMENT, OPTIMIZATION AND LOGGING OF THE EFFECTS OF A THERAPY

(71) Applicant: Ivan Osorio, Leawood, KS (US)

(72) Inventor: Ivan Osorio, Leawood, KS (US)

(73) Assignee: Flint Hills Scientific, L.L.C., Lawrence, KS (US)

(*) Notice: Subject to any disclaimer, the term of this patent is extended or adjusted under 35 U.S.C. 154(b) by 6 days.

(21) Appl. No.: 16/523,159

(22) Filed: Jul. 26, 2019

(65) Prior Publication Data

US 2019/0344078 A1    Nov. 14, 2019

Related U.S. Application Data

(60) Continuation of application No. 15/586,433, filed on May 4, 2017, now Pat. No. 10,406,364, which is a
(Continued)

(51) Int. Cl.
*A61N 1/36* (2006.01)
*A61B 5/0476* (2006.01)
(Continued)

(52) U.S. Cl.
CPC ........ *A61N 1/36064* (2013.01); *A61B 5/0476* (2013.01); *A61B 5/4094* (2013.01);
(Continued)

(58) Field of Classification Search
CPC ............ A61N 1/36064; A61N 1/36114; A61N 1/36139; A61N 1/36146; A61N 1/0529;
(Continued)

(56) References Cited

U.S. PATENT DOCUMENTS

| 2005/0197590 | A1* | 9/2005 | Osorio | A61B 5/4094 600/544 |
|---|---|---|---|---|
| 2006/0017749 | A1* | 1/2006 | McIntyre | A61N 1/36082 345/664 |

(Continued)

*Primary Examiner* — Amanda K Hulbert
*Assistant Examiner* — Natasha Patel
(74) *Attorney, Agent, or Firm* — CF3; Stephen Eisenmann

(57) ABSTRACT

A method for assessment, optimization and logging of the effects of a therapy for a medical condition, including (a) receiving into a signal processor input signals indicative of the subject's brain activity; (b) characterizing the spatio-temporal behavior of the brain activity using the signals; (c) delivering a therapy to a target tissue of the subject; (d) characterizing the spatio-temporal effect of the therapy on the brain activity; (e) in response to the characterizing, optimizing at least one parameter of the therapy if the brain activity has not been satisfactorily modified and/or has been adversely modified by the therapy; (f) characterizing the spatio-temporal effect of the at least one optimized parameter; and (g) logging to memory the at least one optimized parameter. A computer readable program storage unit encoded with instructions that, when executed by a computer, performs the method.

10 Claims, 41 Drawing Sheets

Figure 1:
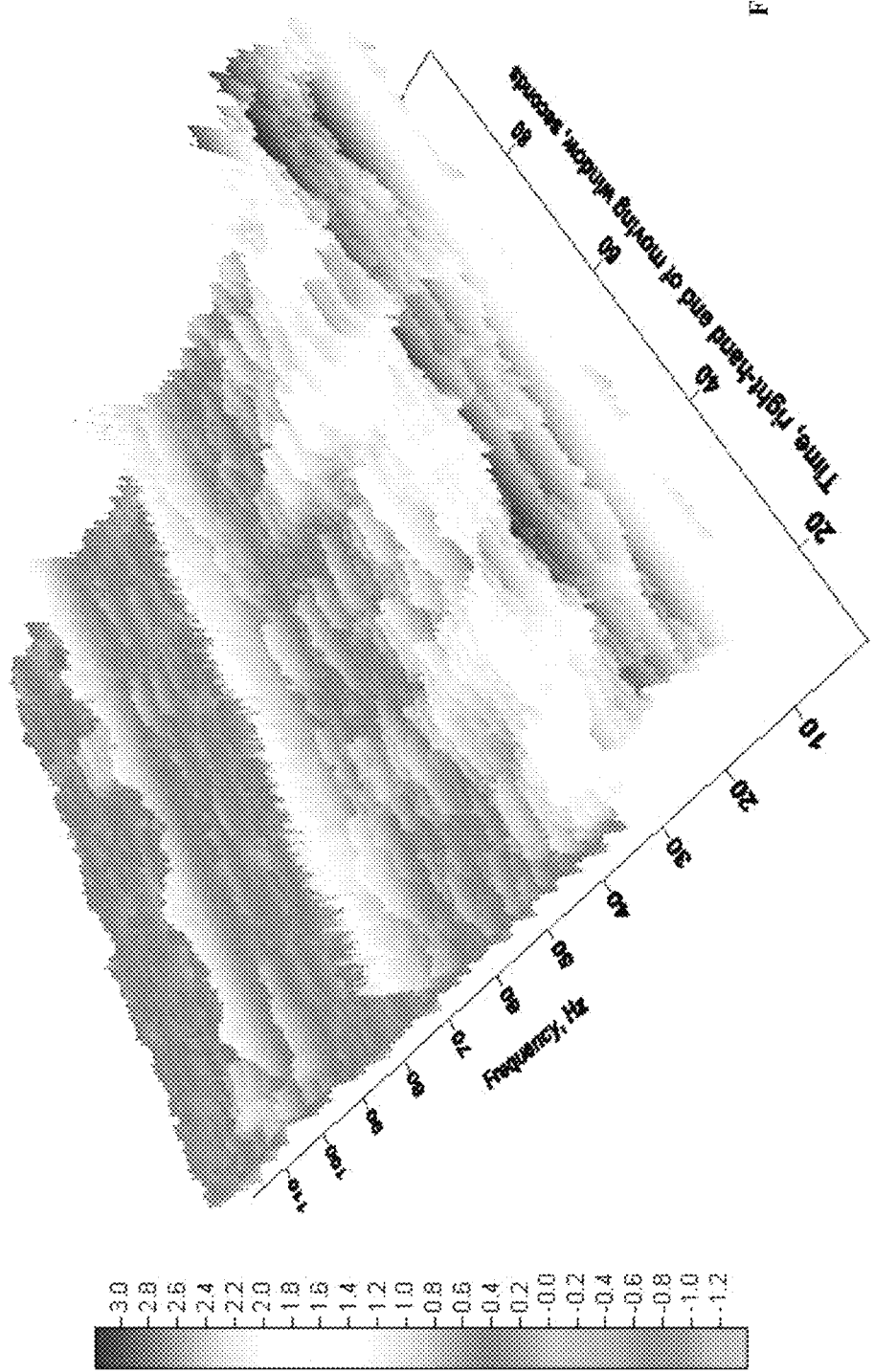
Figure 2:
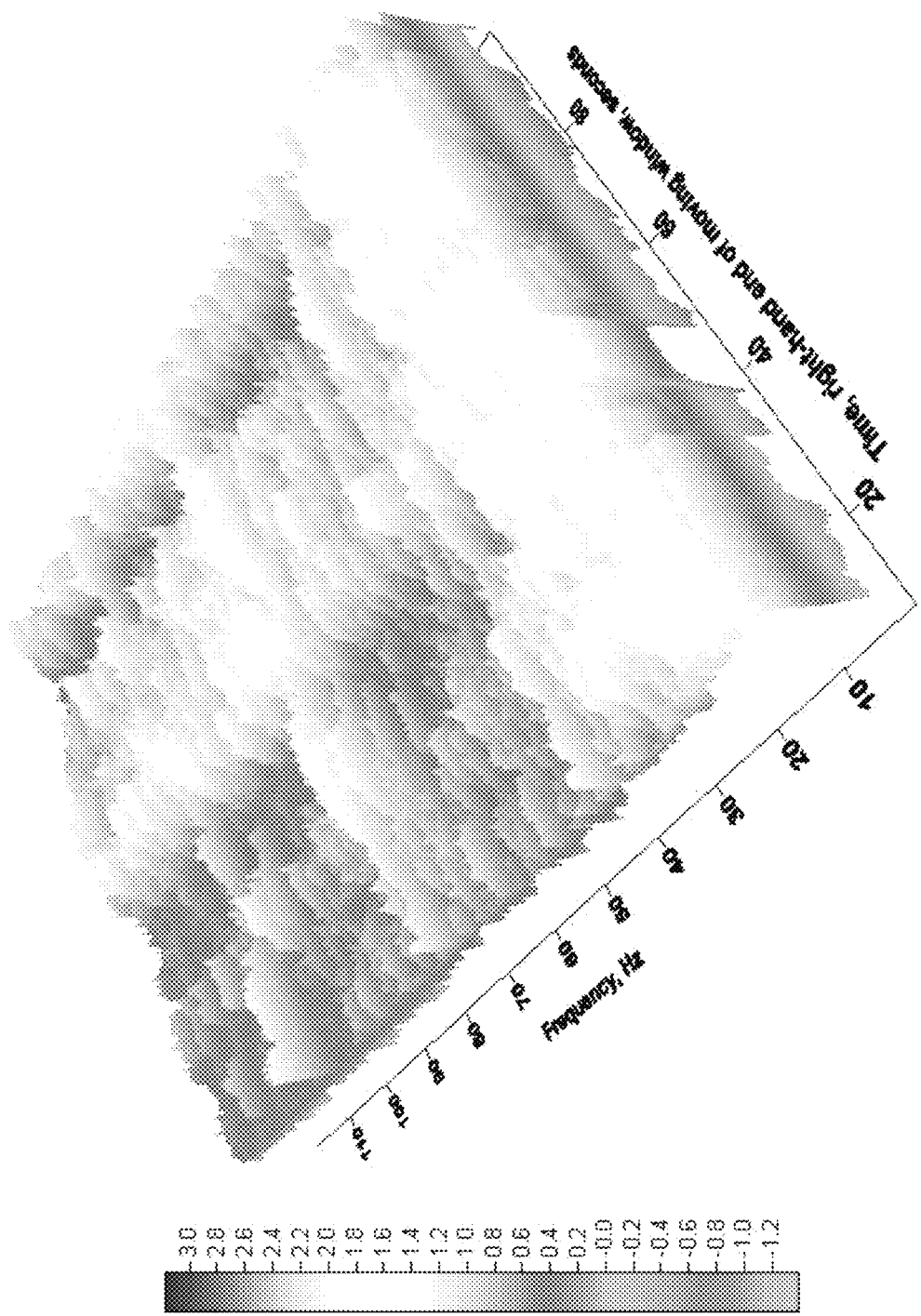
Figure 3:
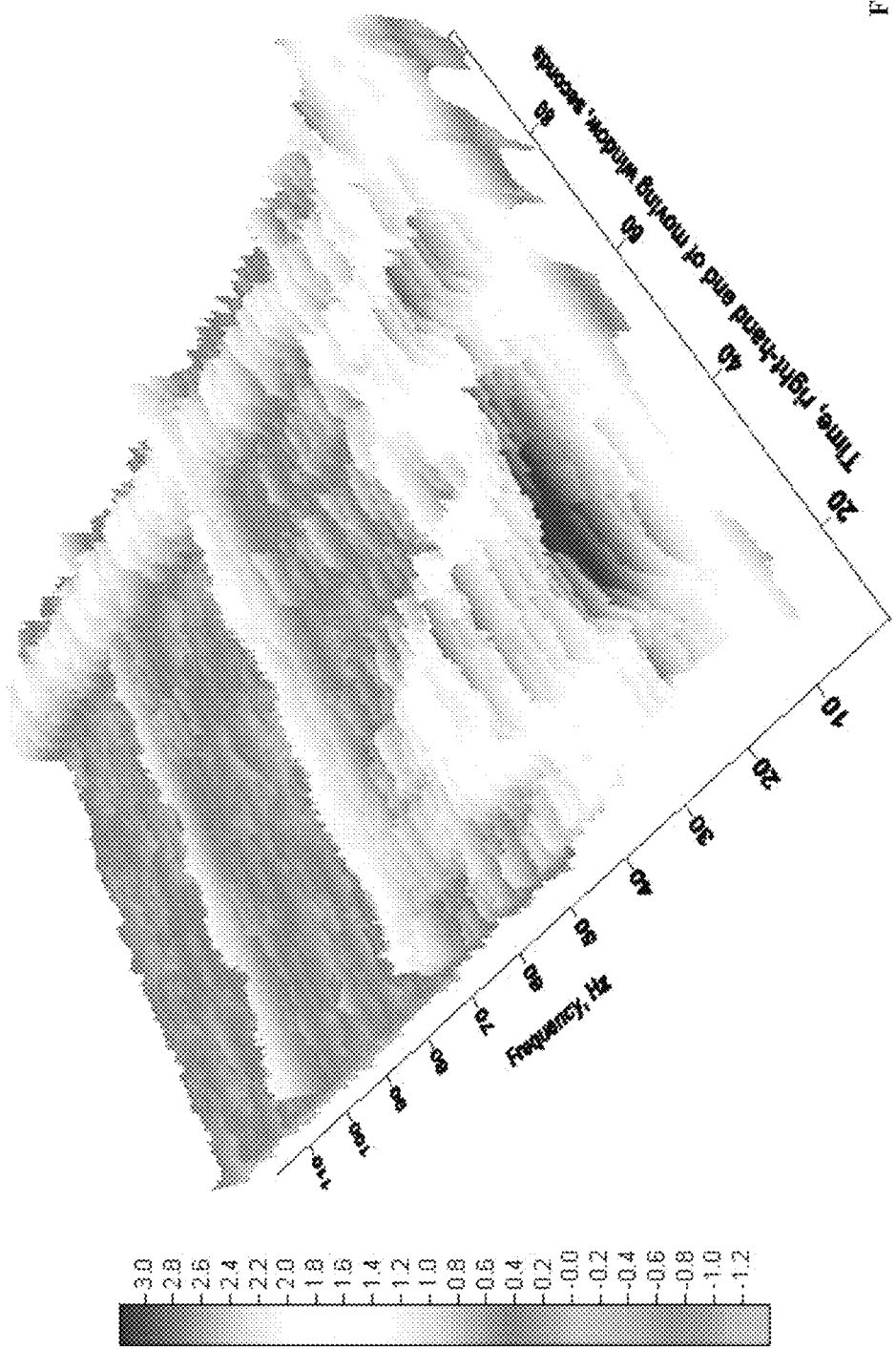
Figure 4:
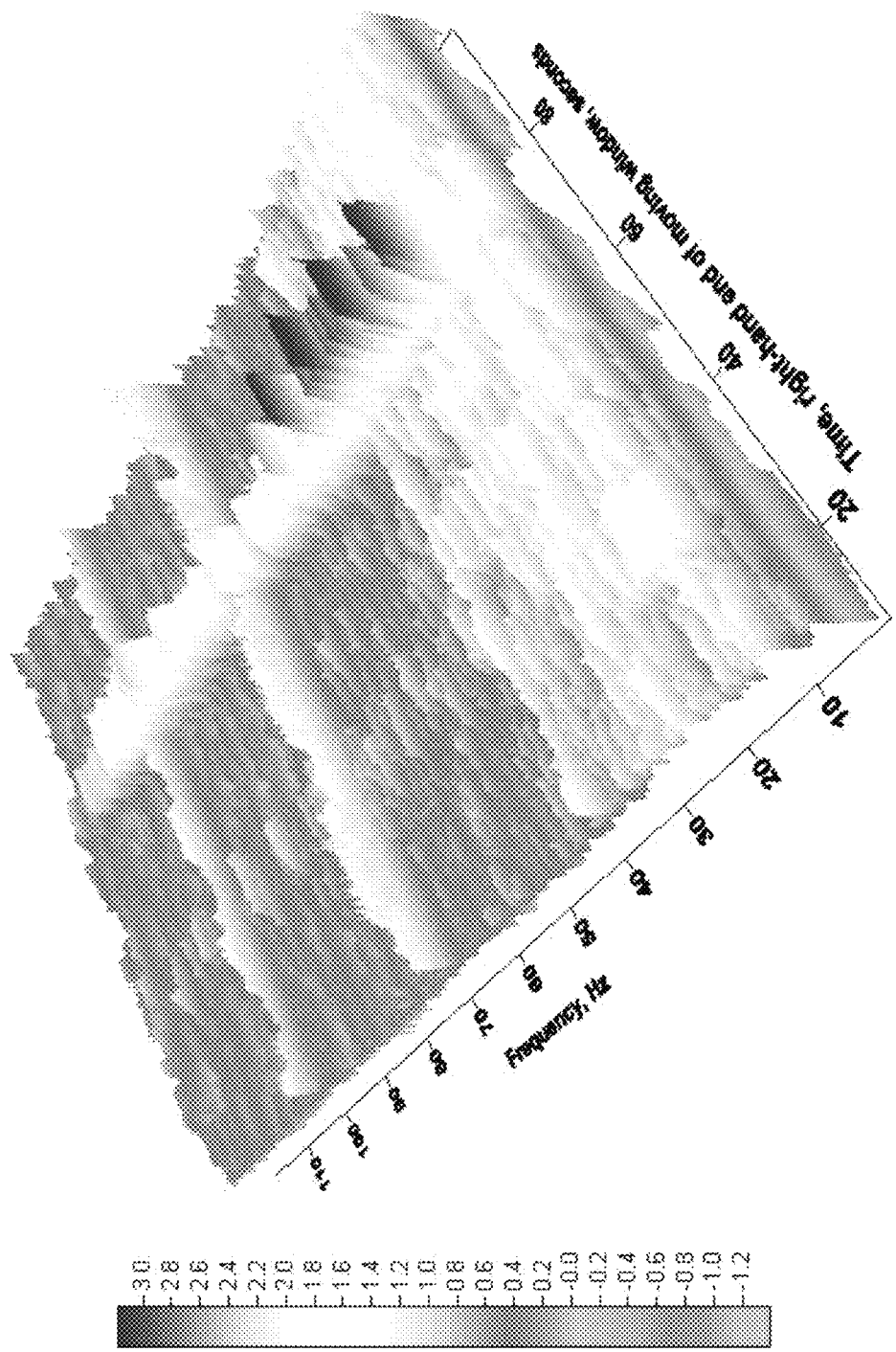
Figure 5:
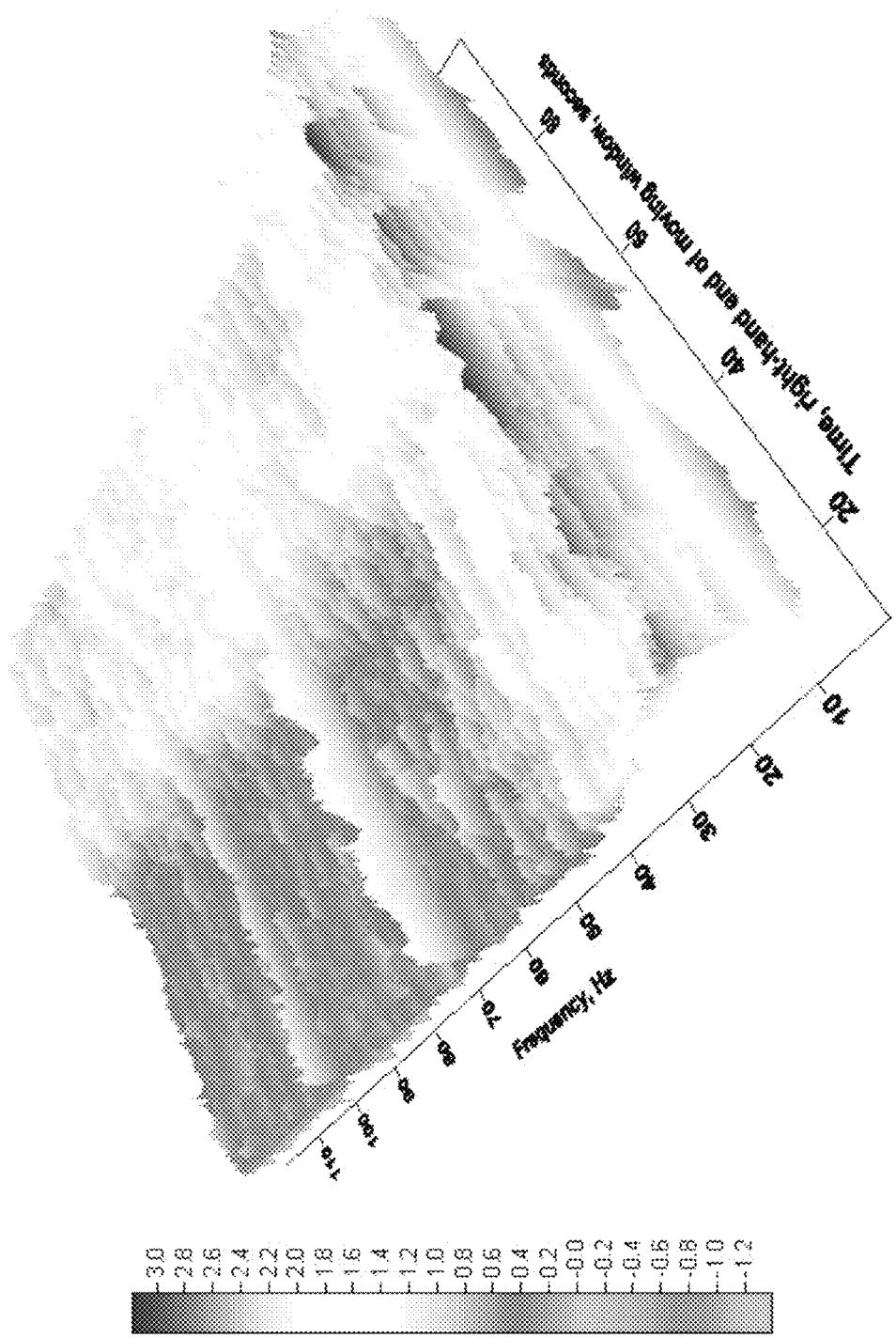
Figure 6:
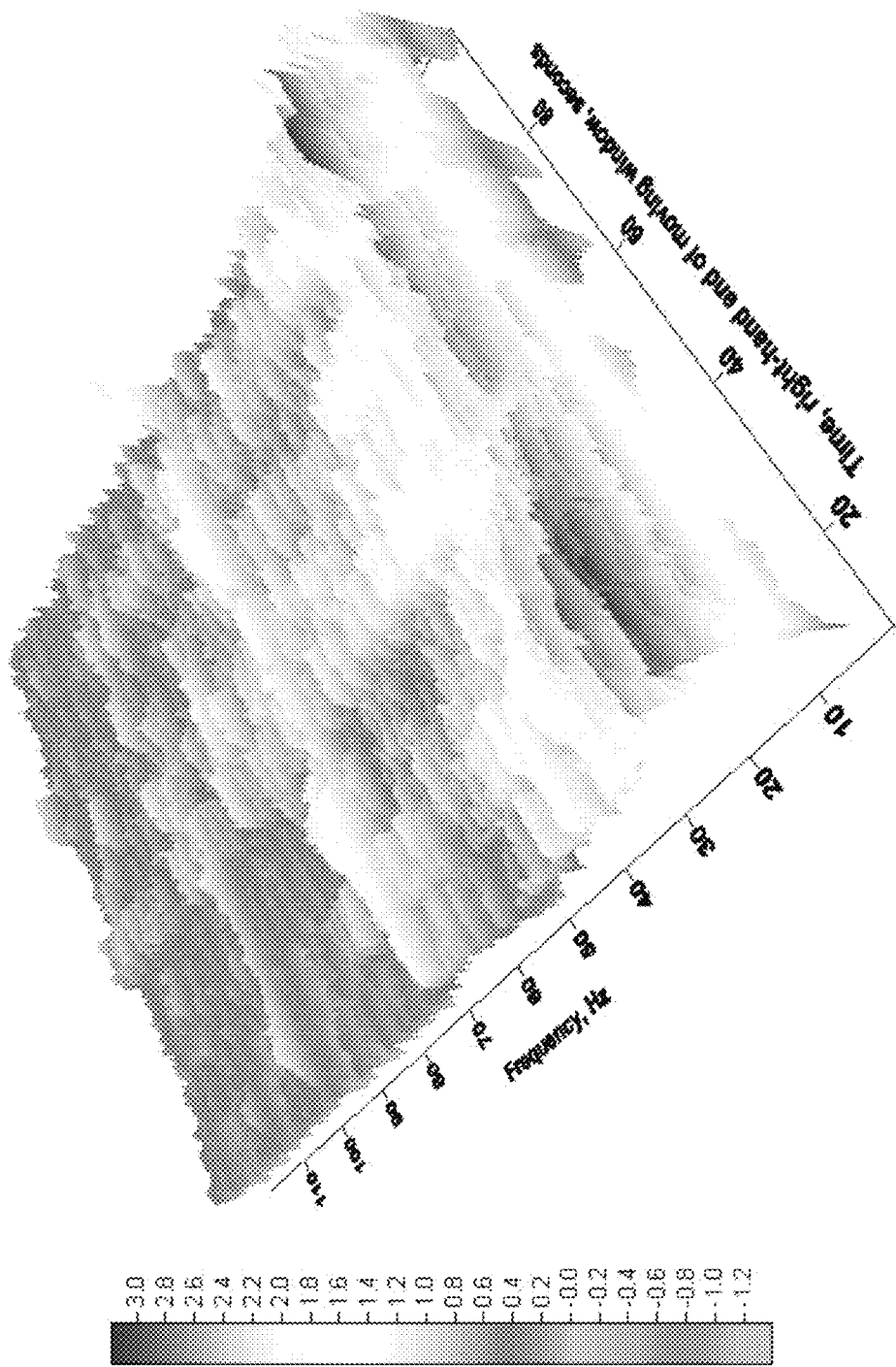
Figure 7:
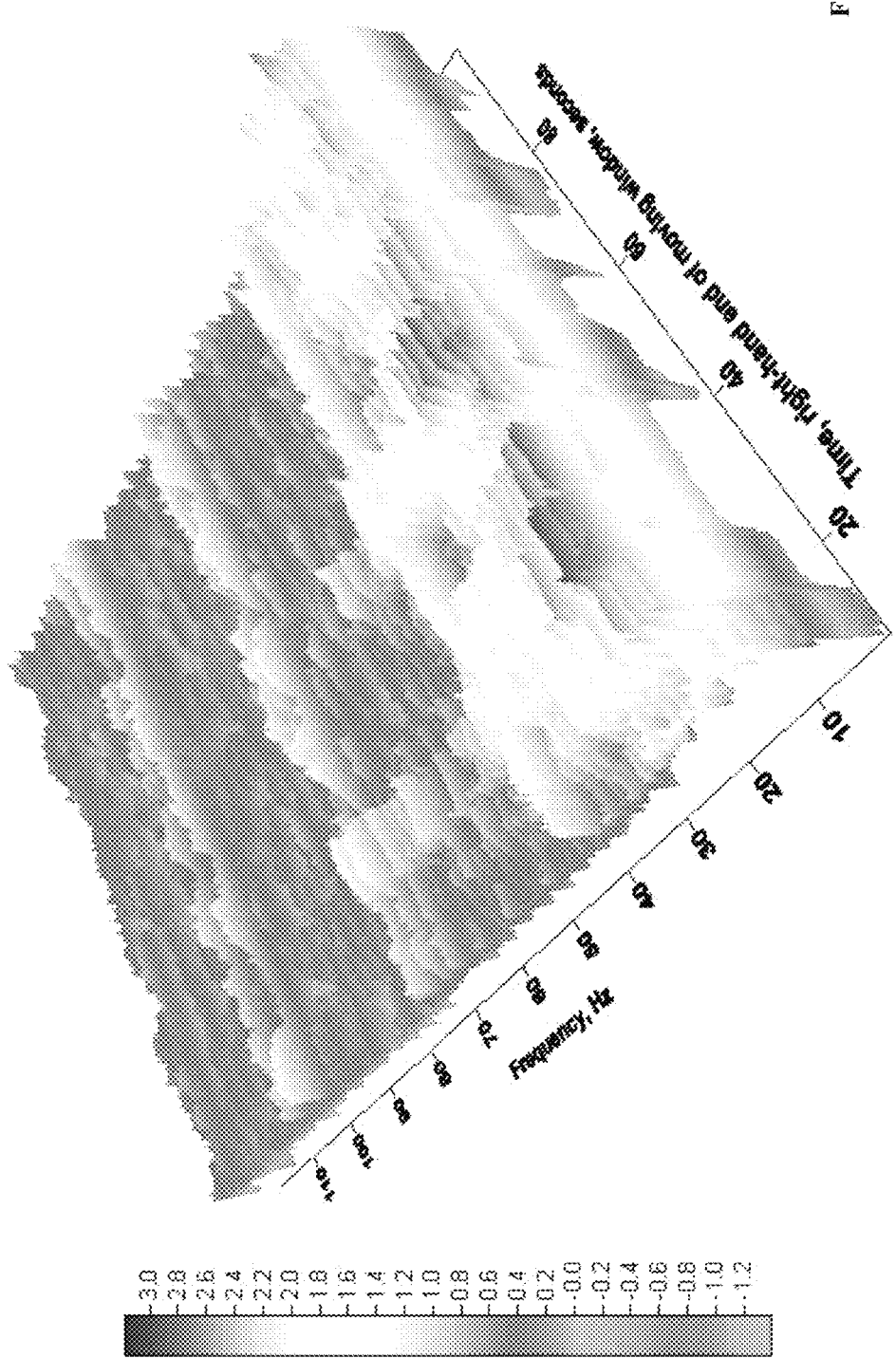
Figure 8:
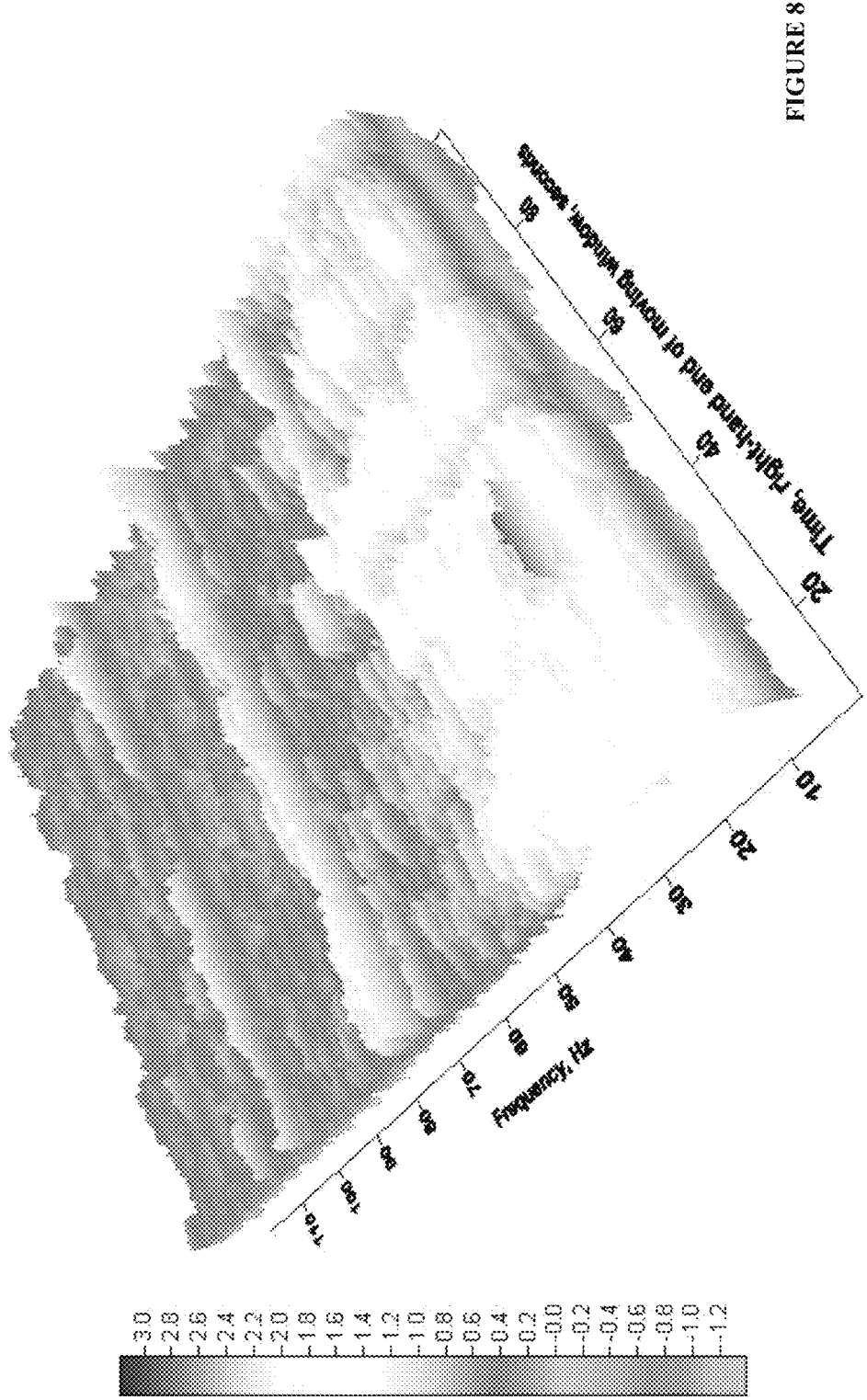
Figure 9:
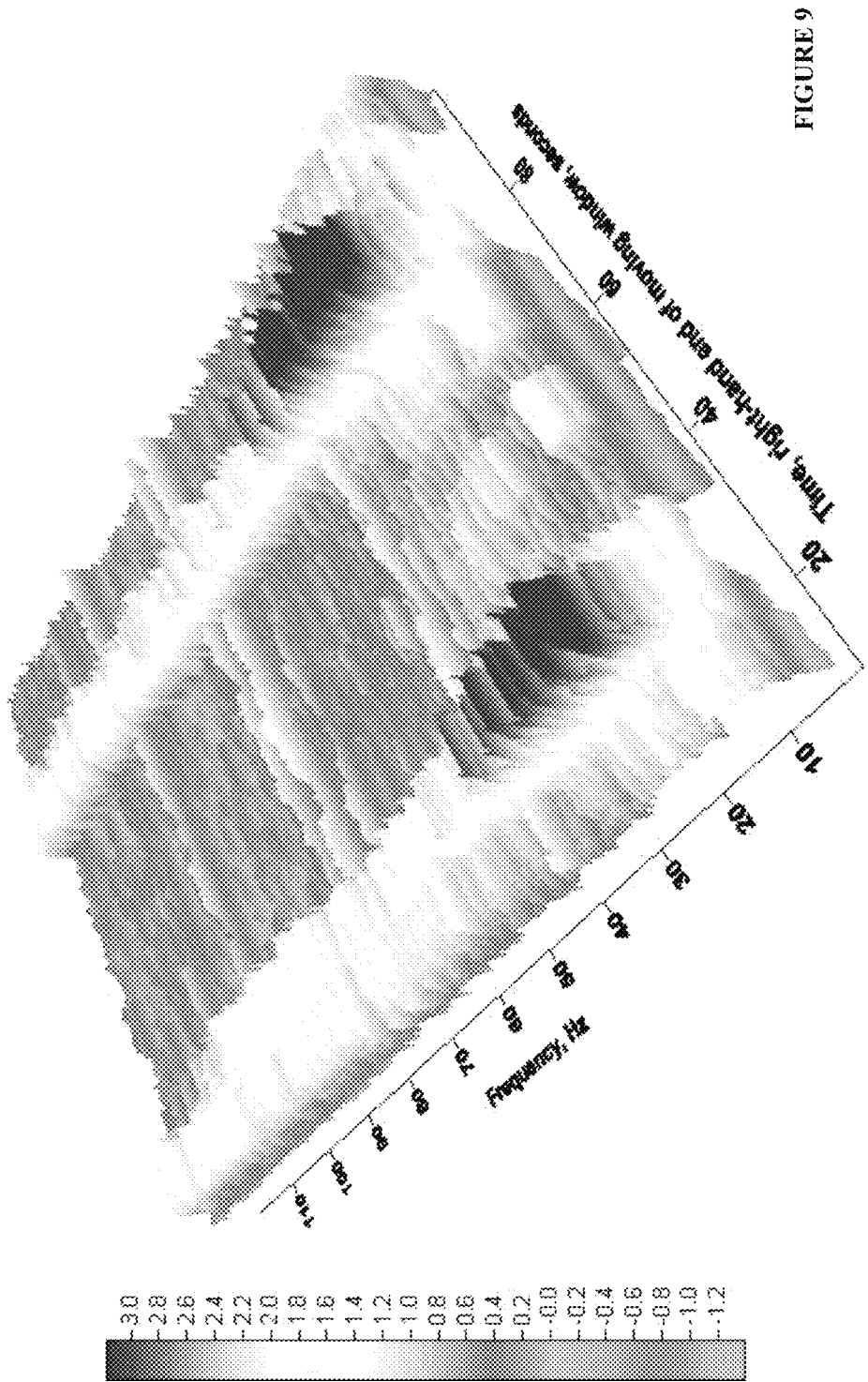
Figure 10:
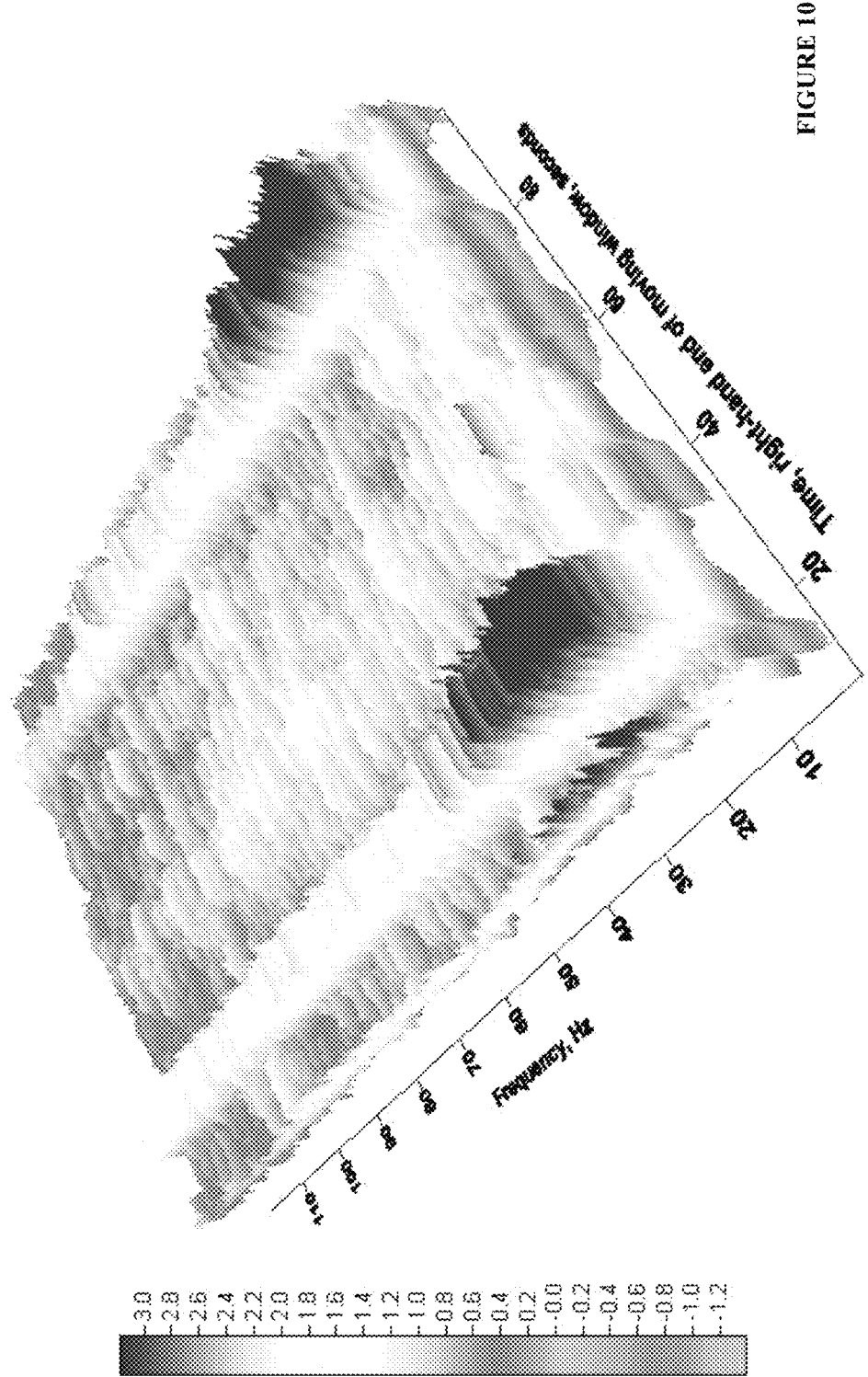
Figure 11:
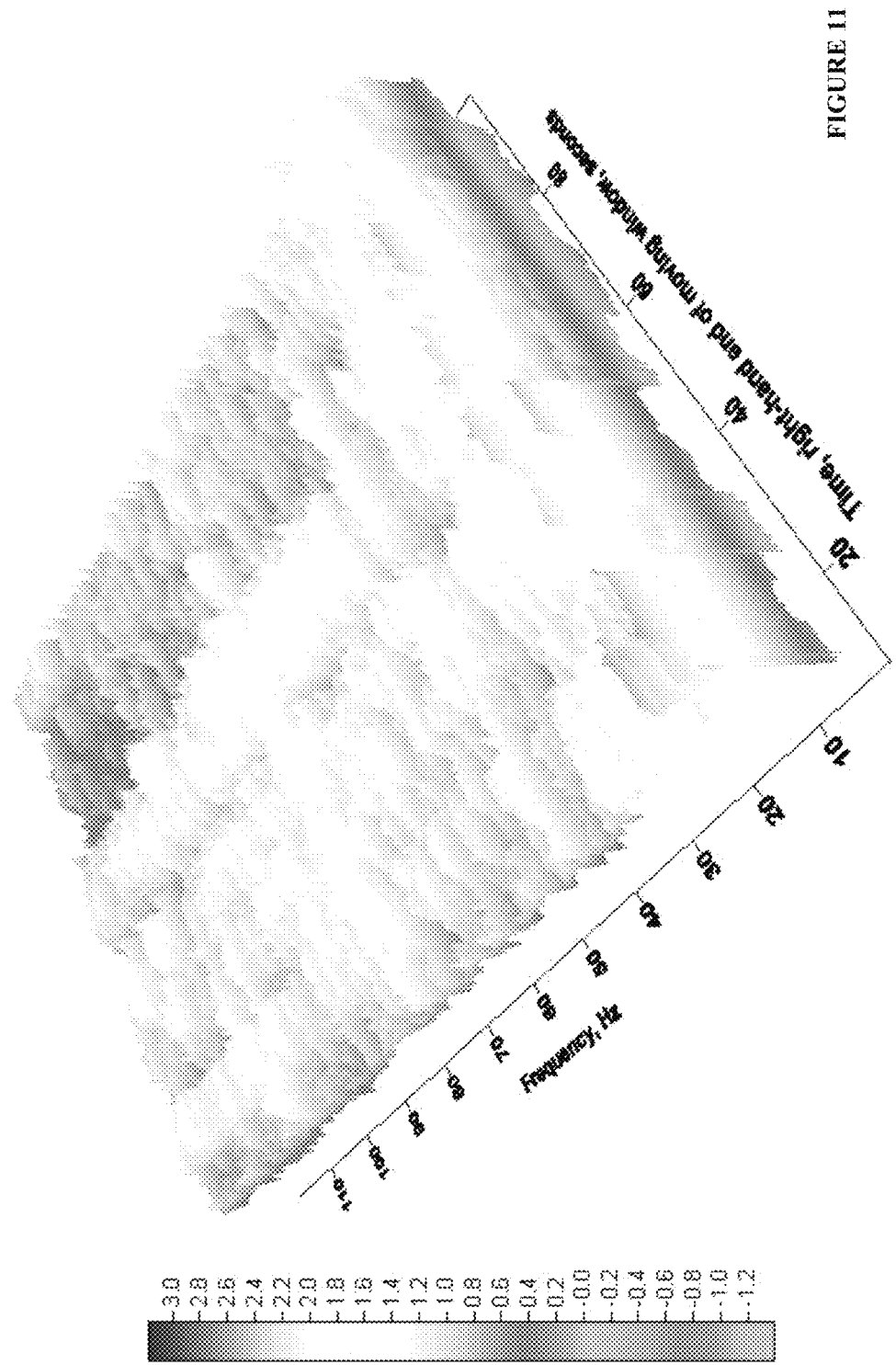
Figure 12:
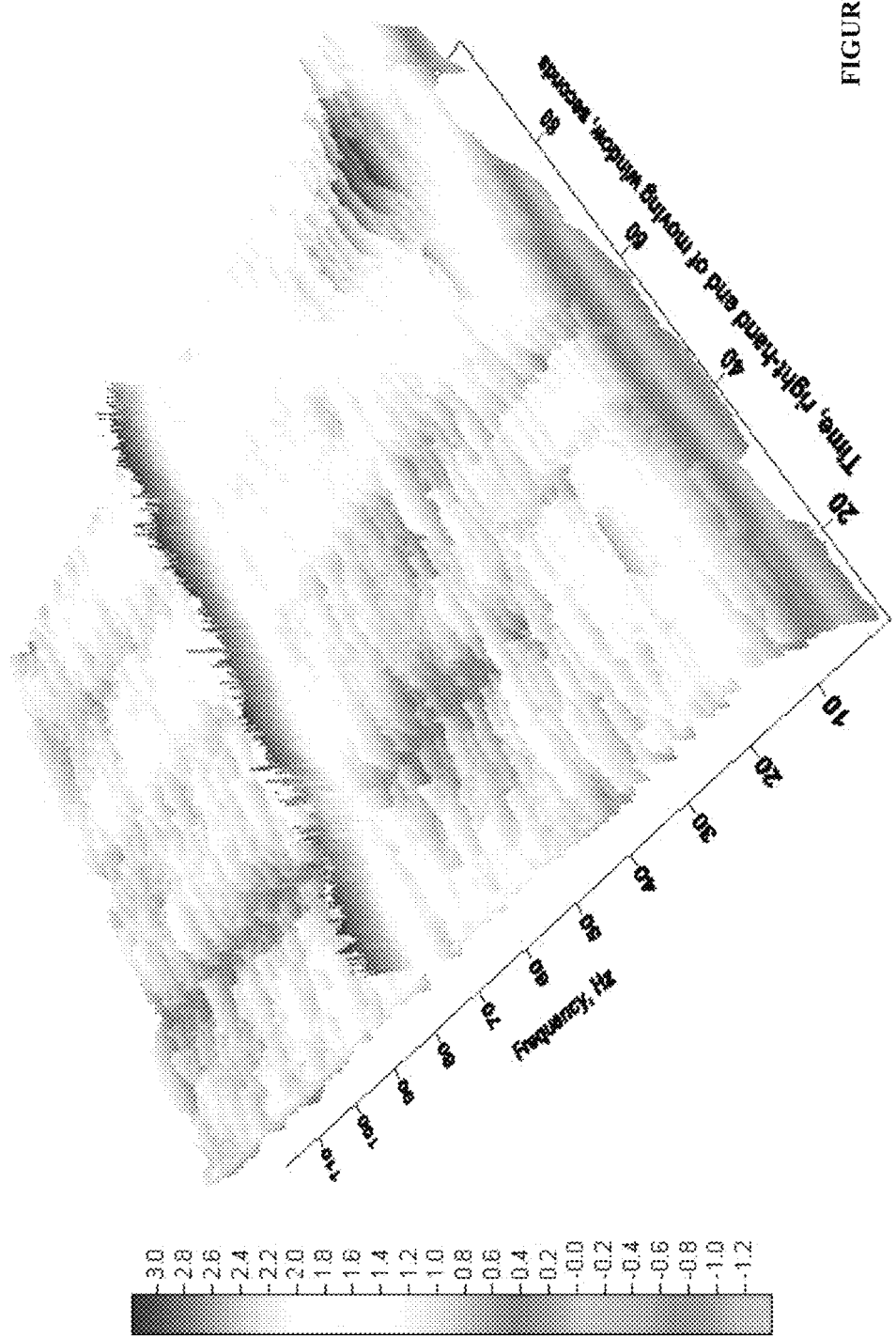
Figure 13:
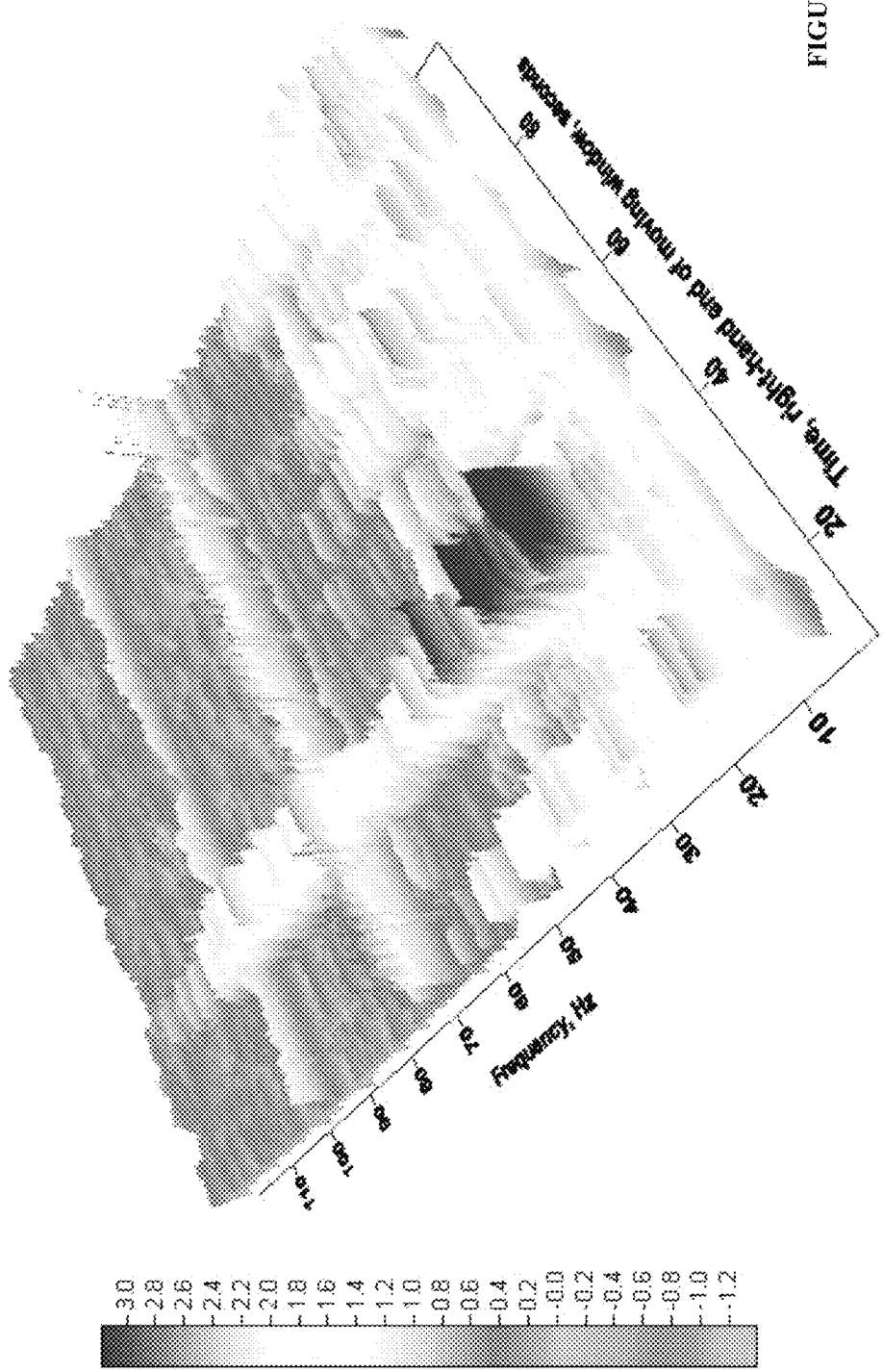
Figure 14:
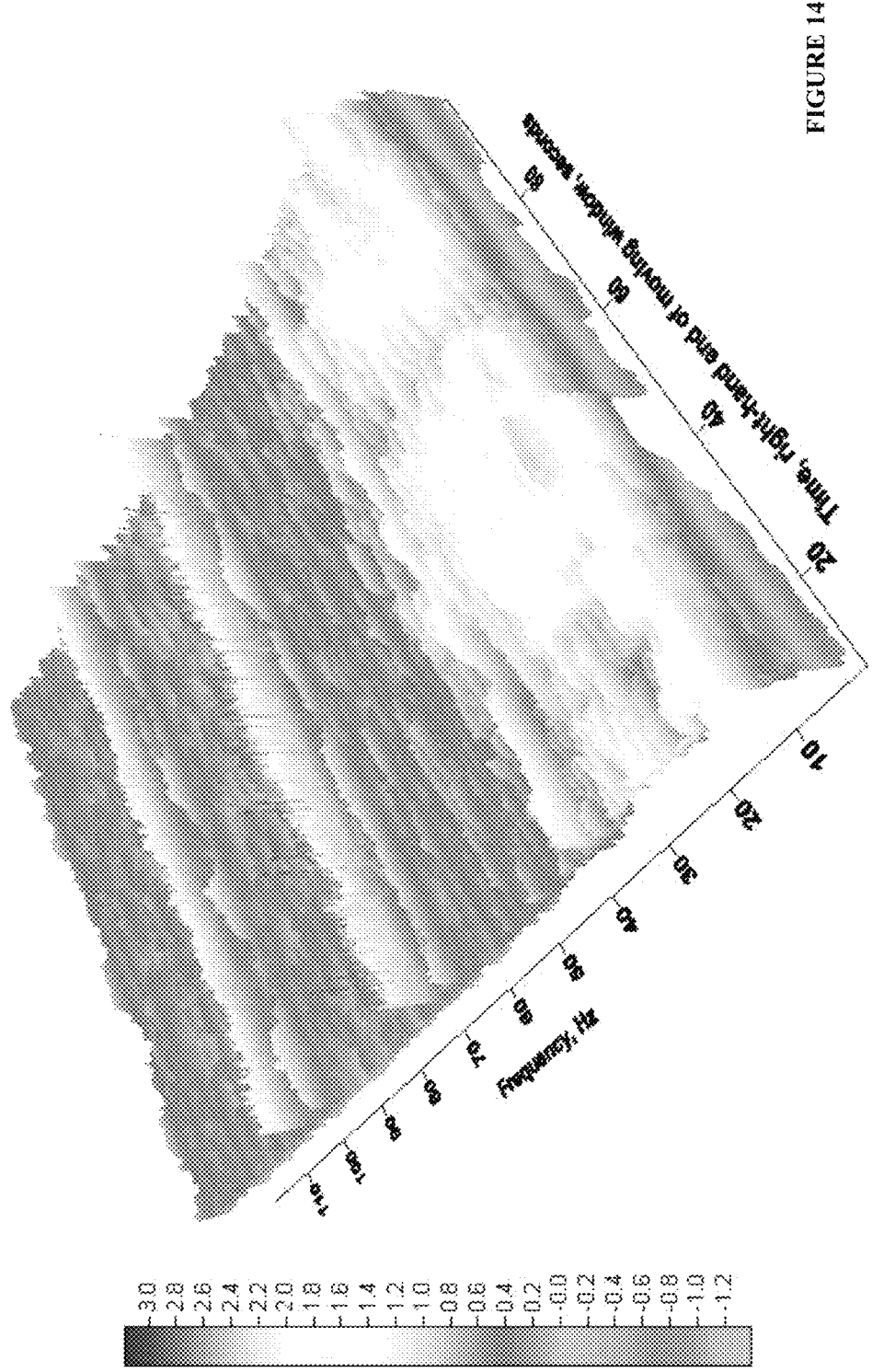
Figure 15:
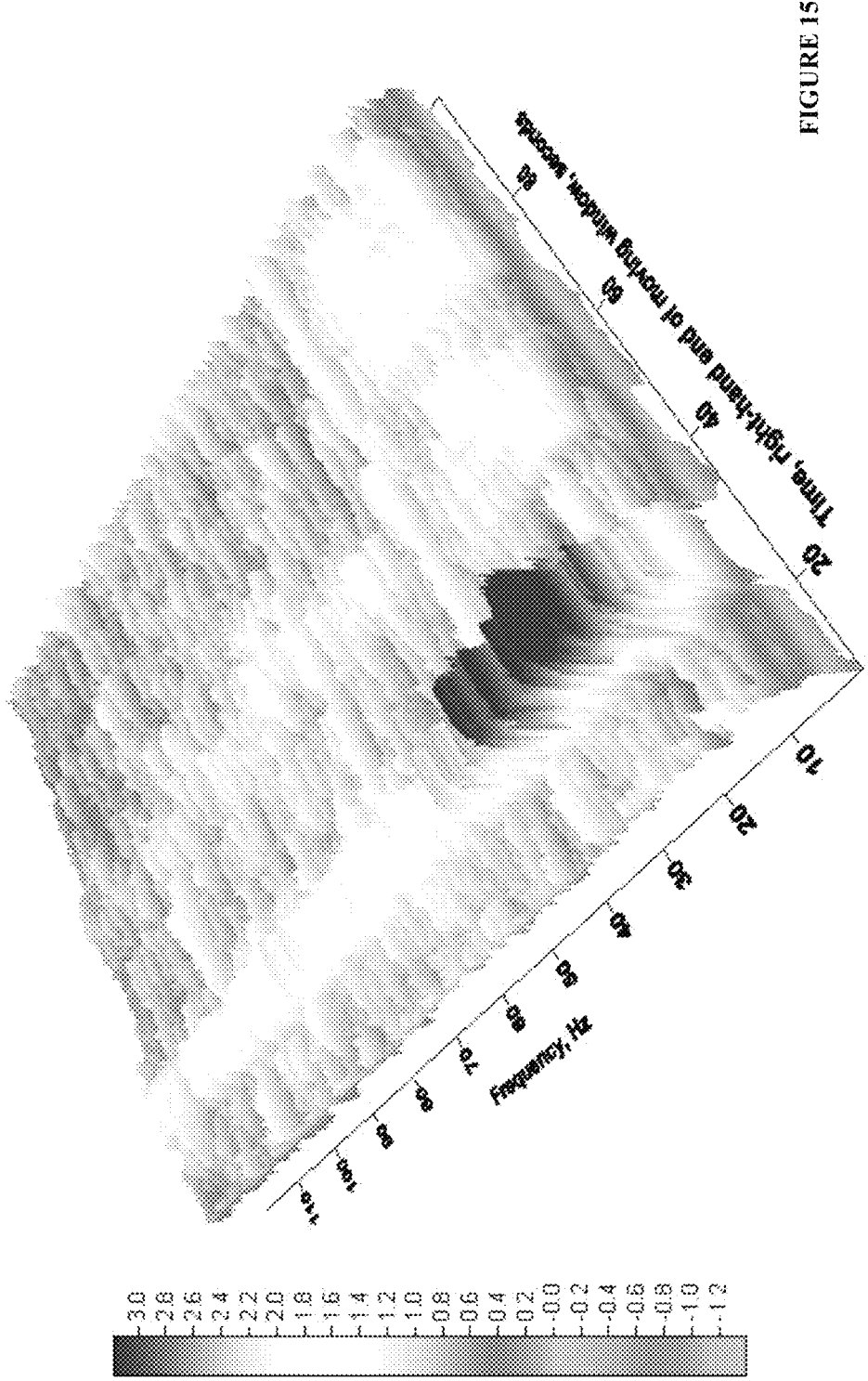
Figure 16:
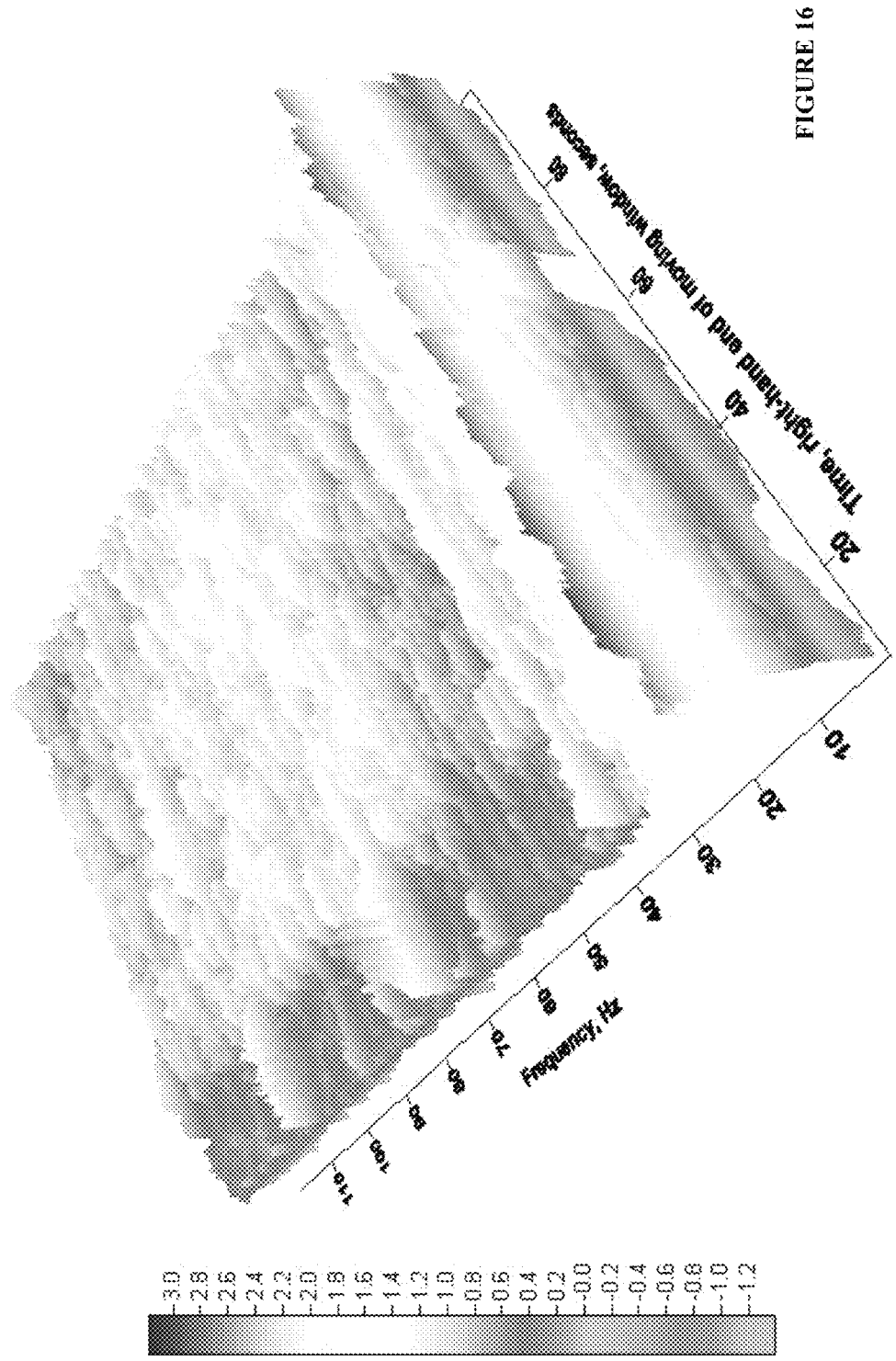
Figure 17:
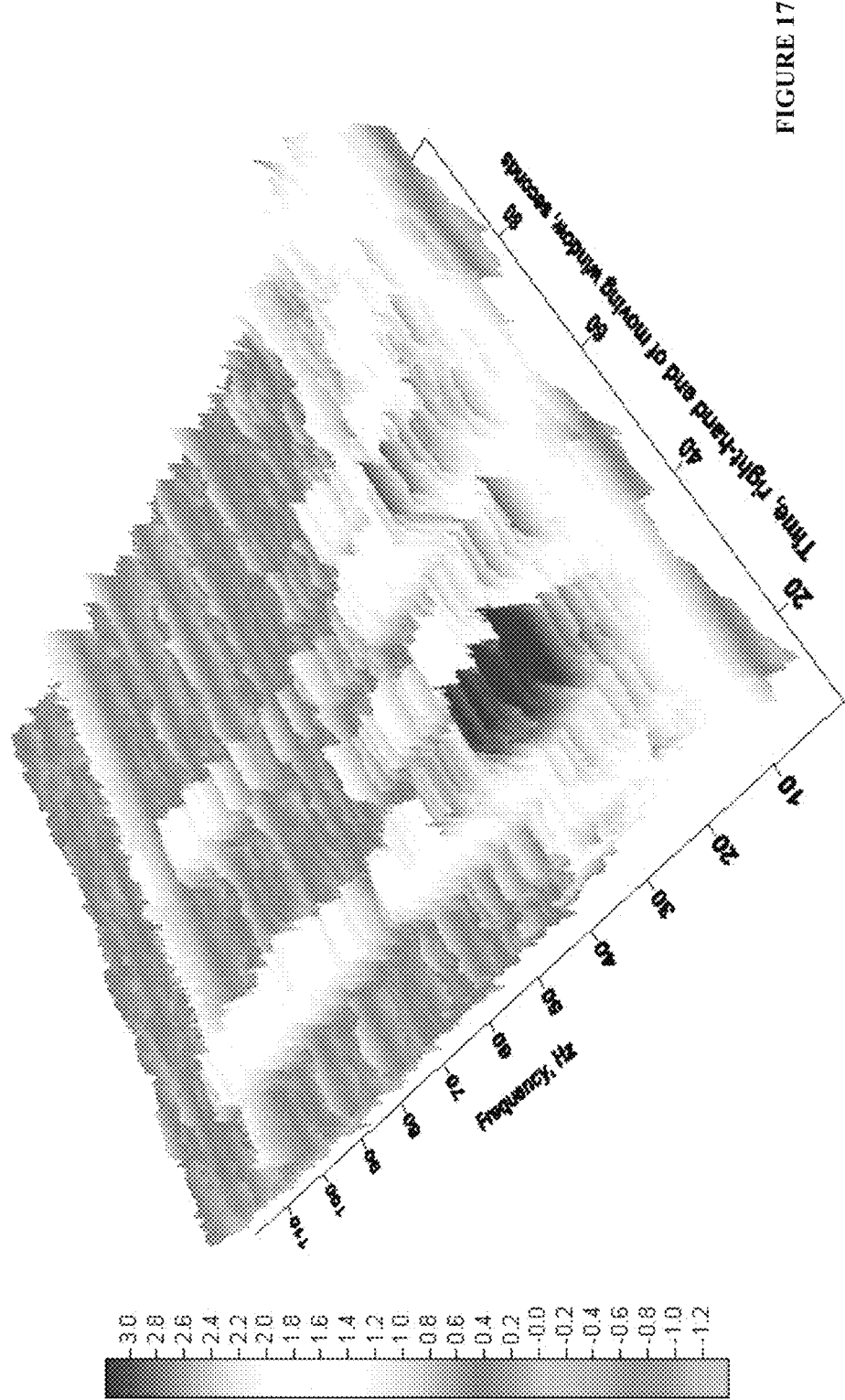
Figure 18:
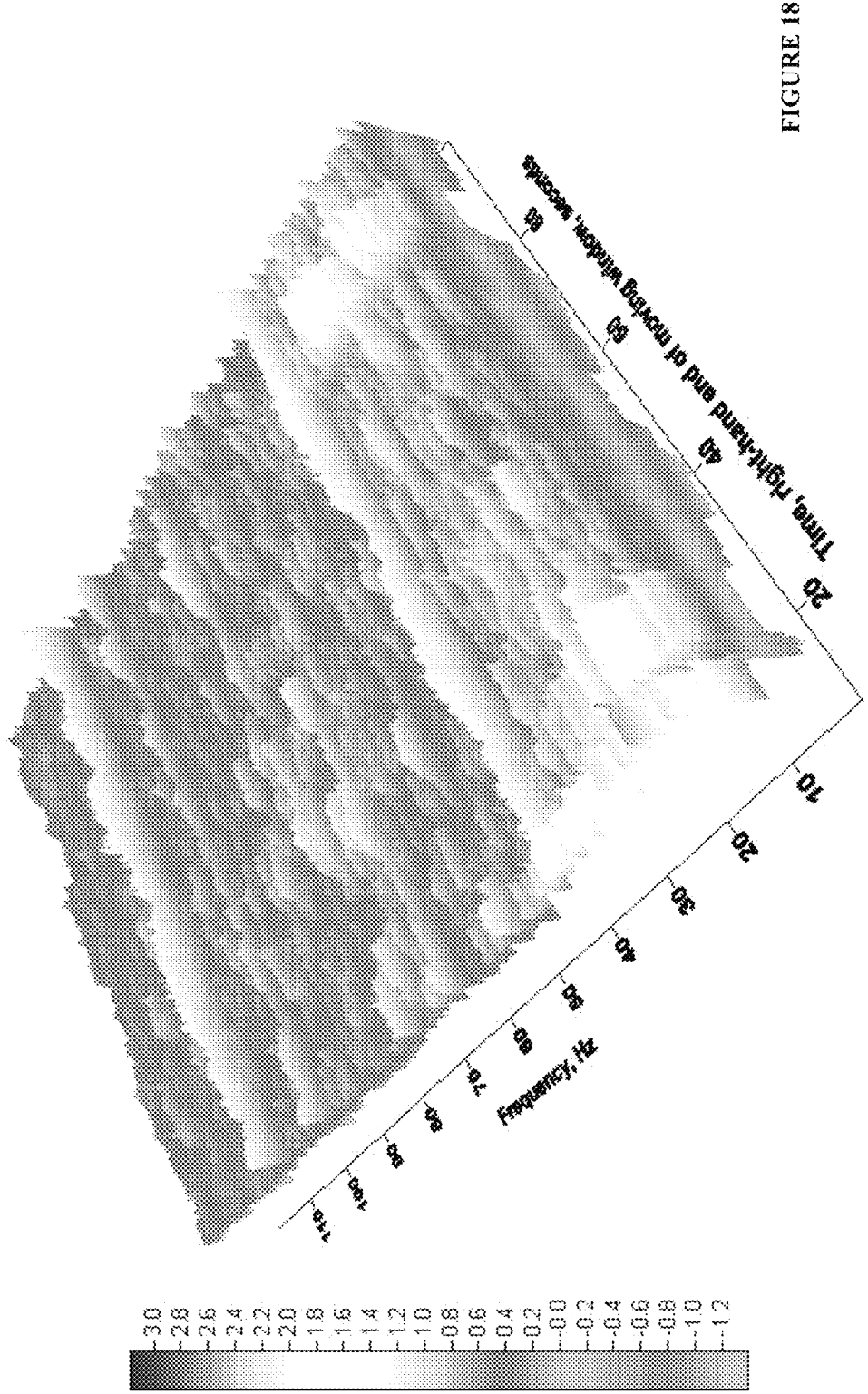
Figure 19:
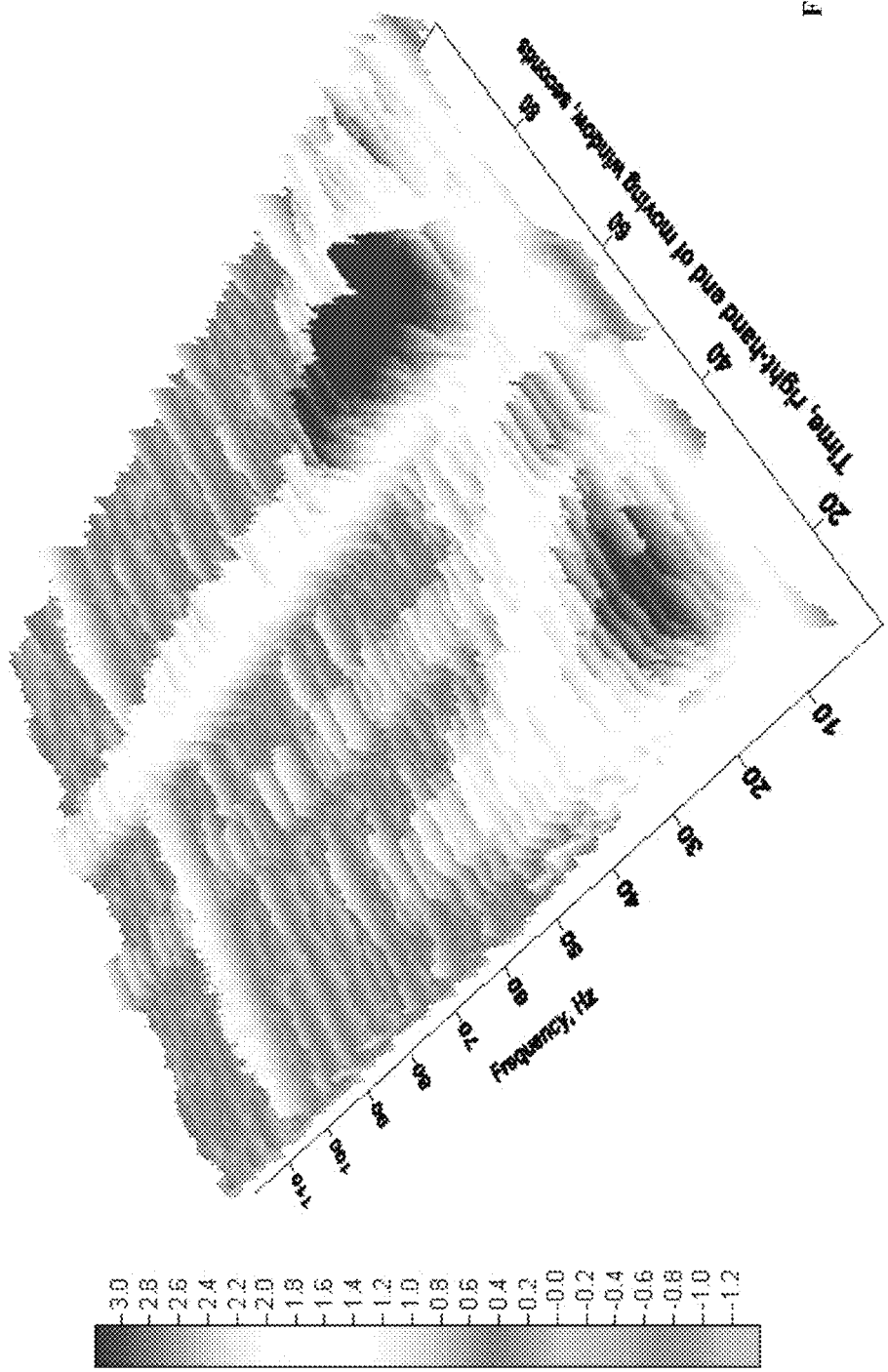
Figure 20:
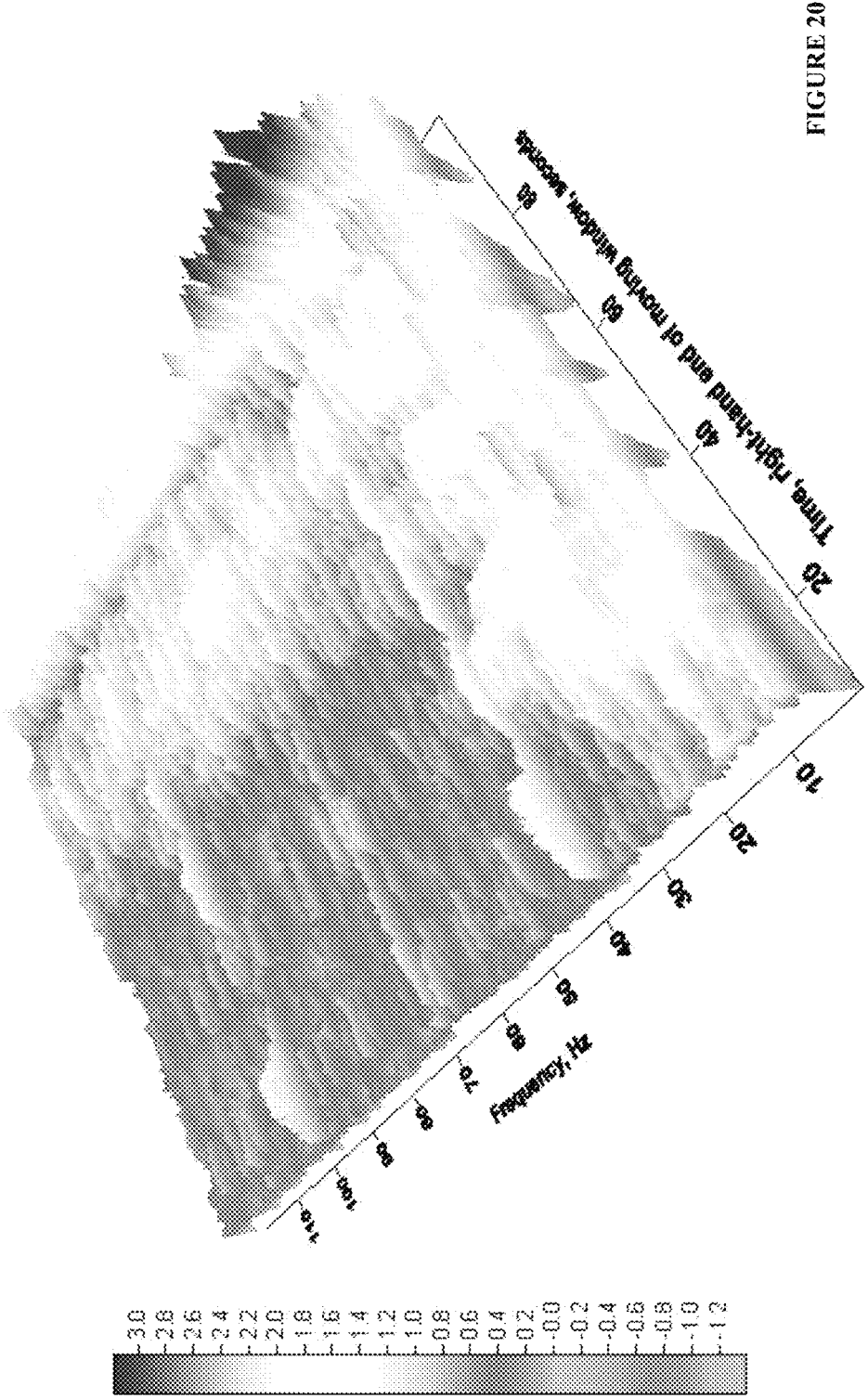
Figure 21:
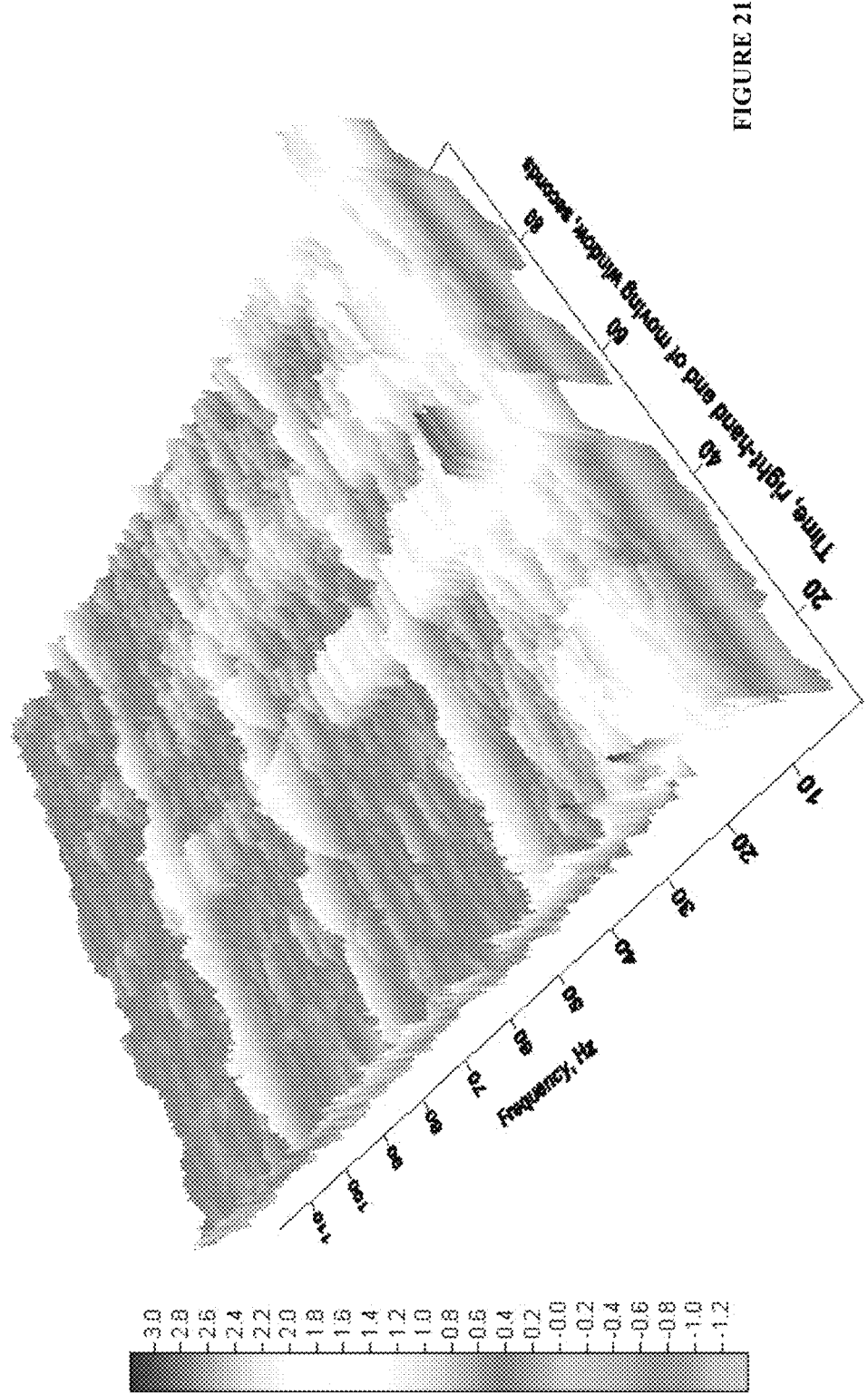
Figure 22:
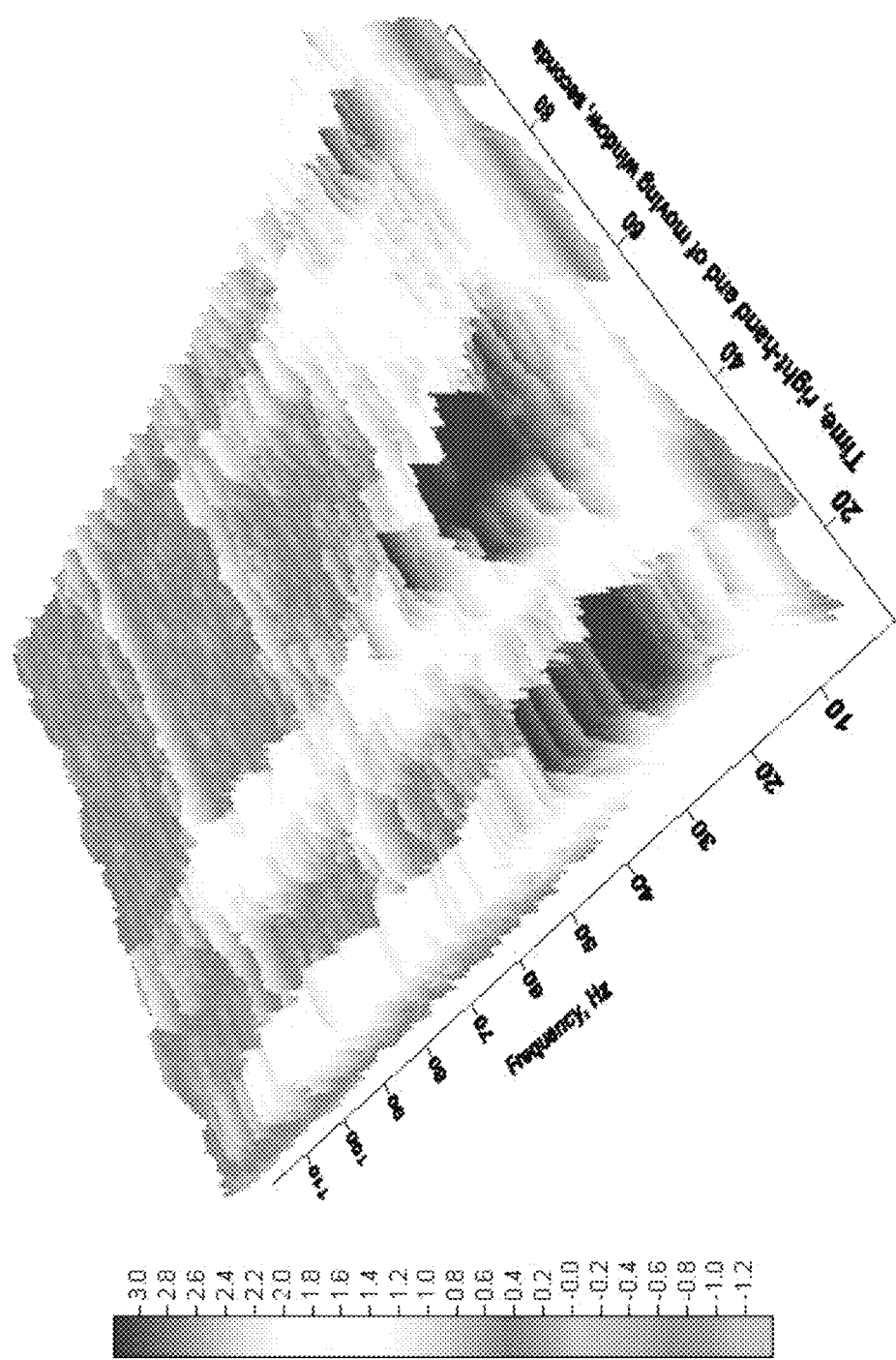
Figure 23:
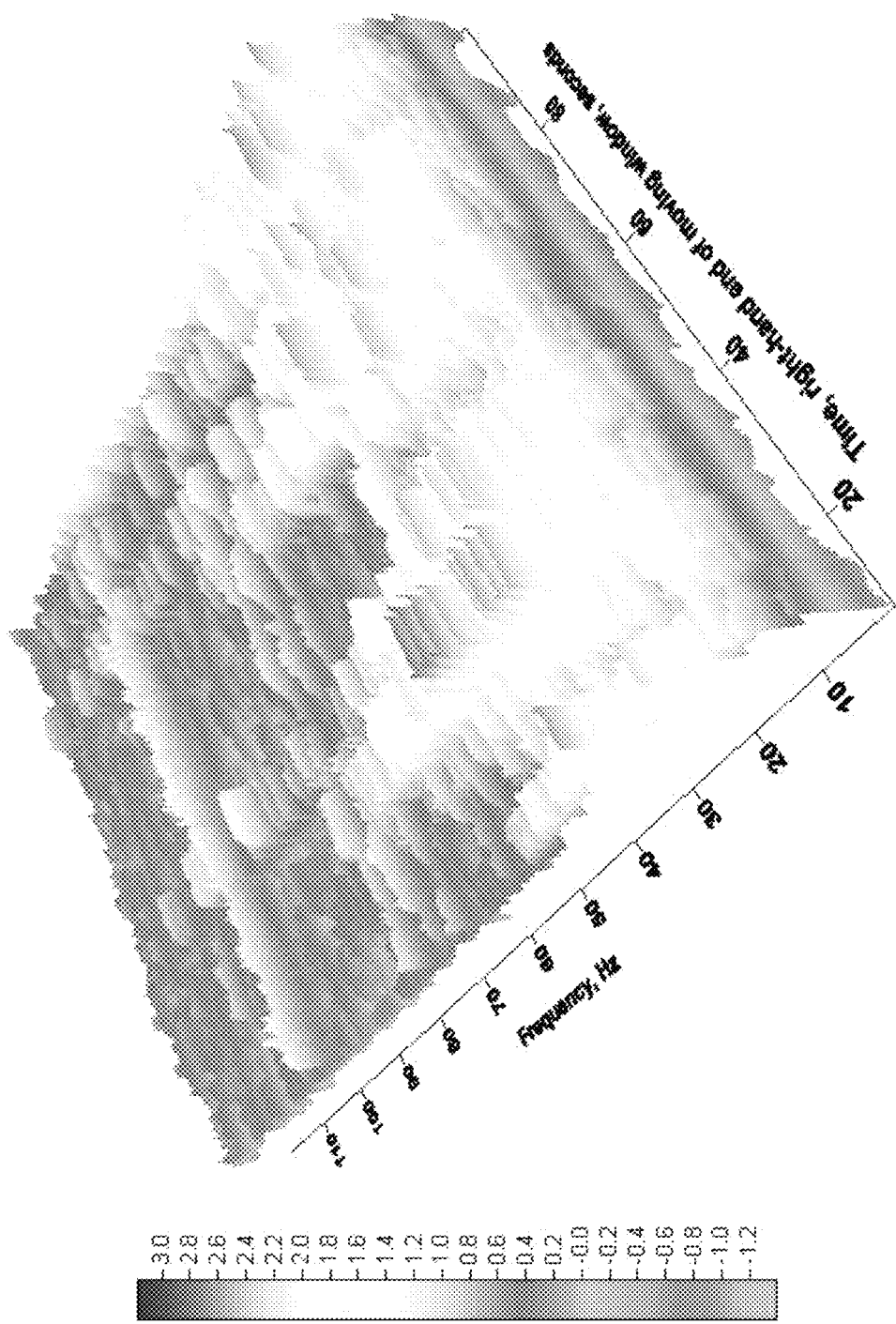
Figure 24:
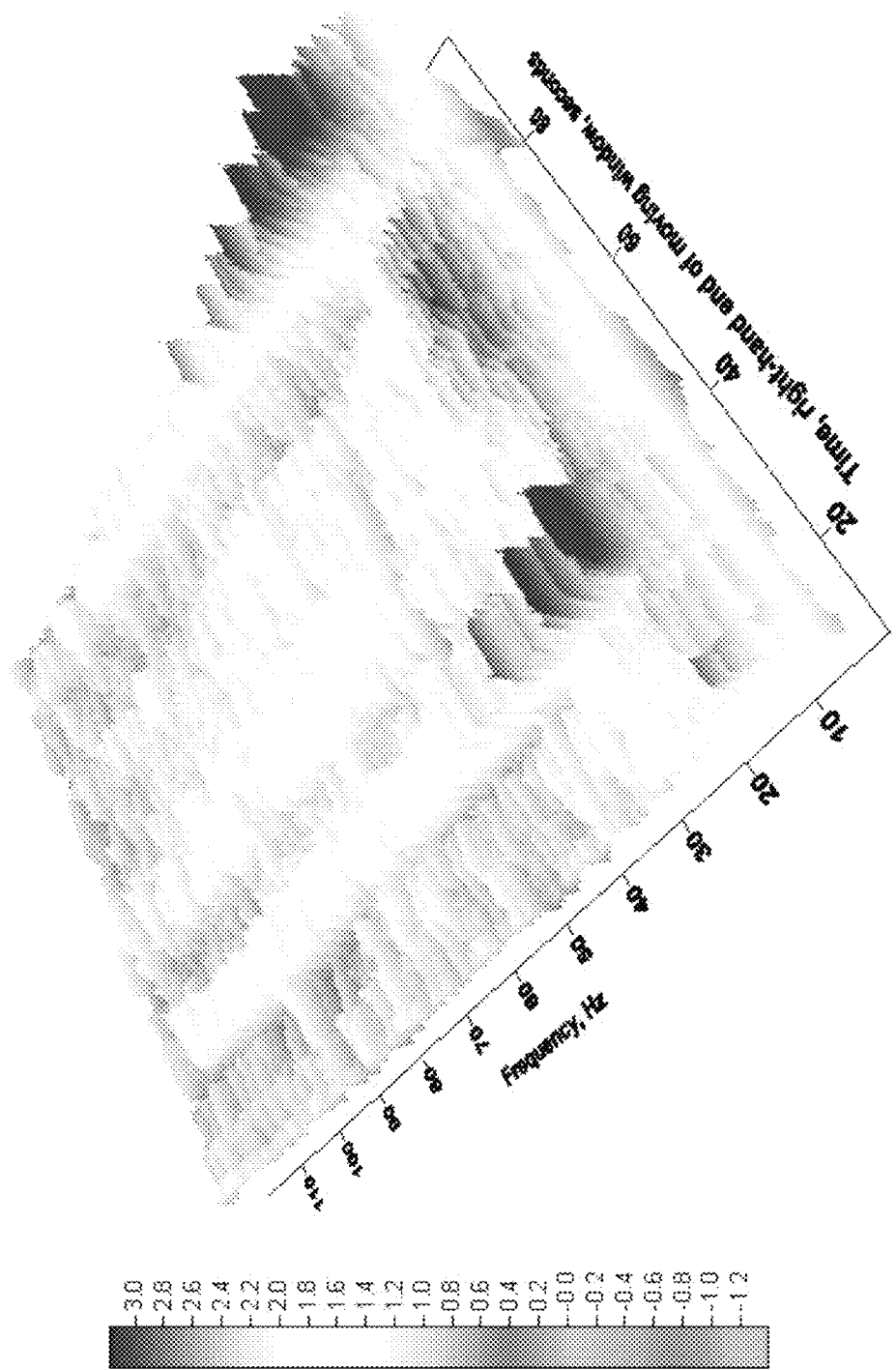
Figure 25:
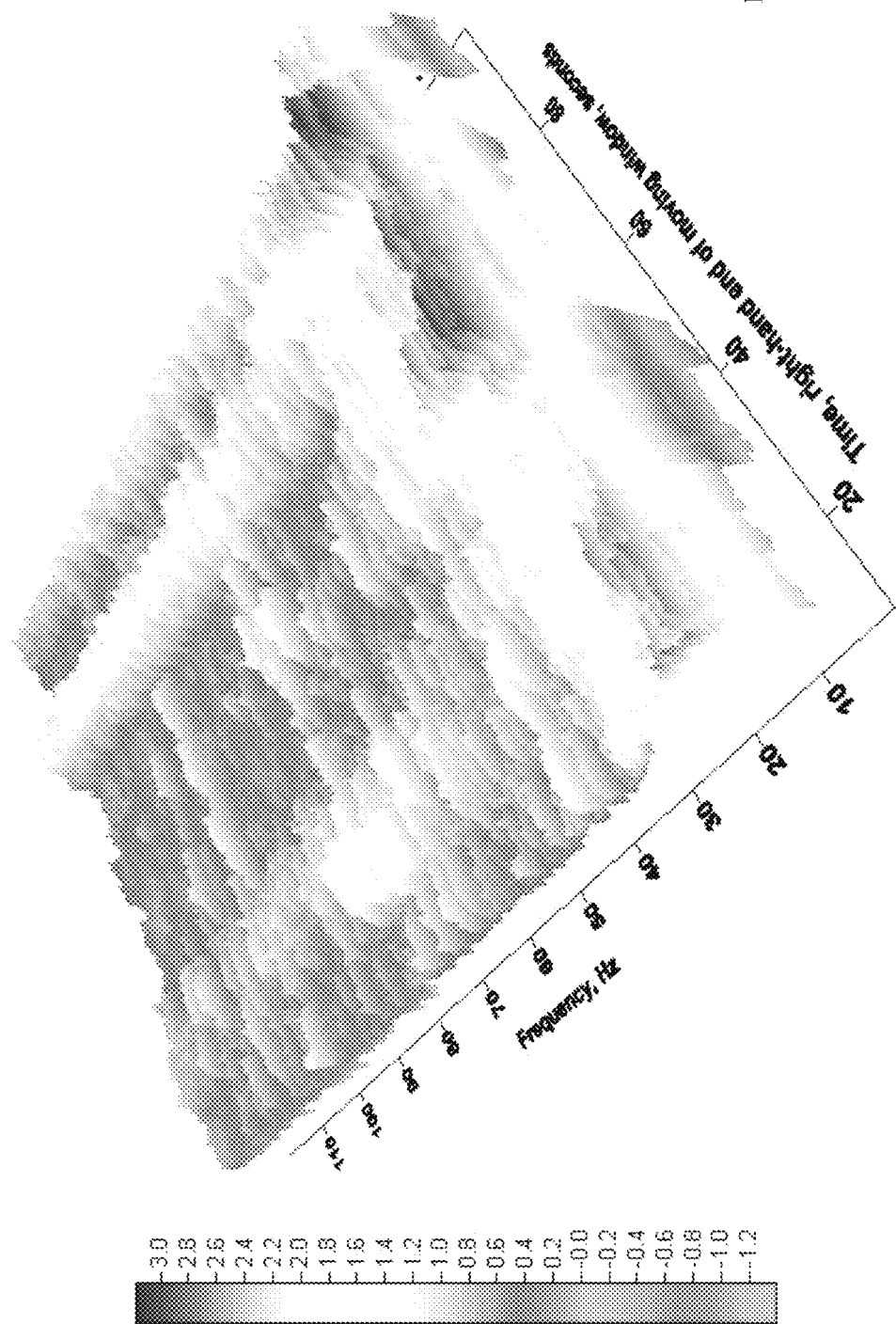
Figure 26:
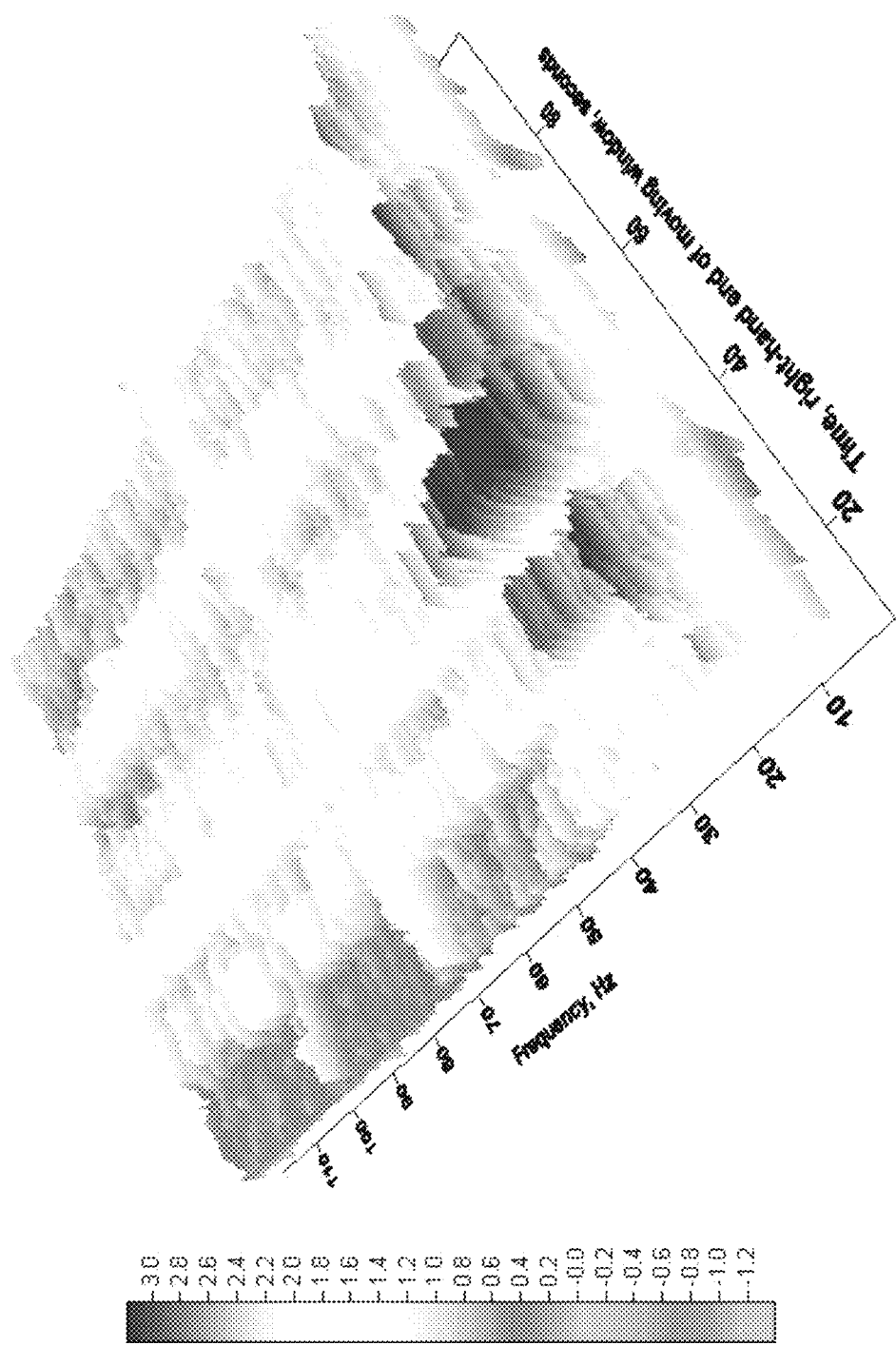
Figure 27:
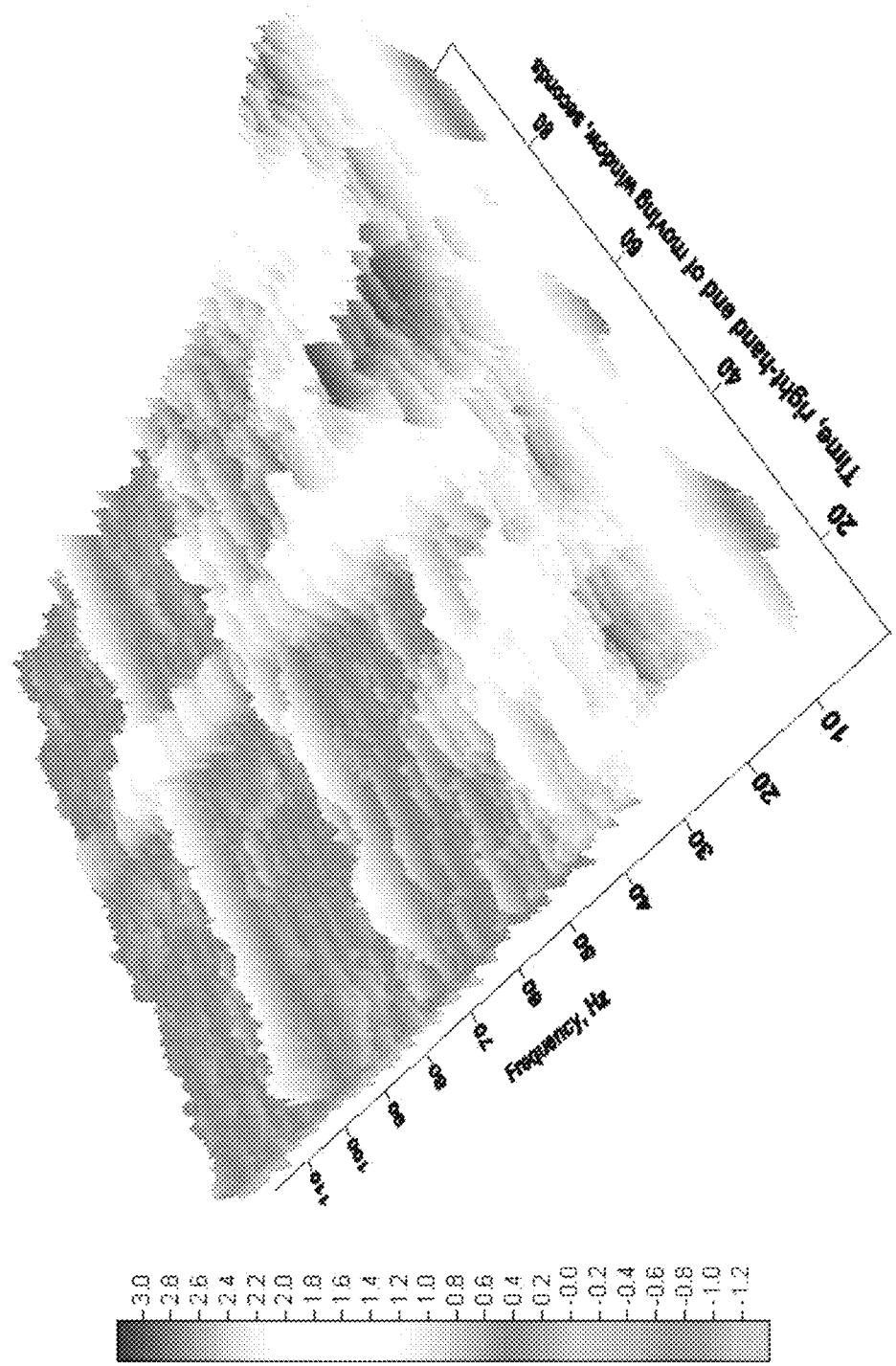
Figure 28:
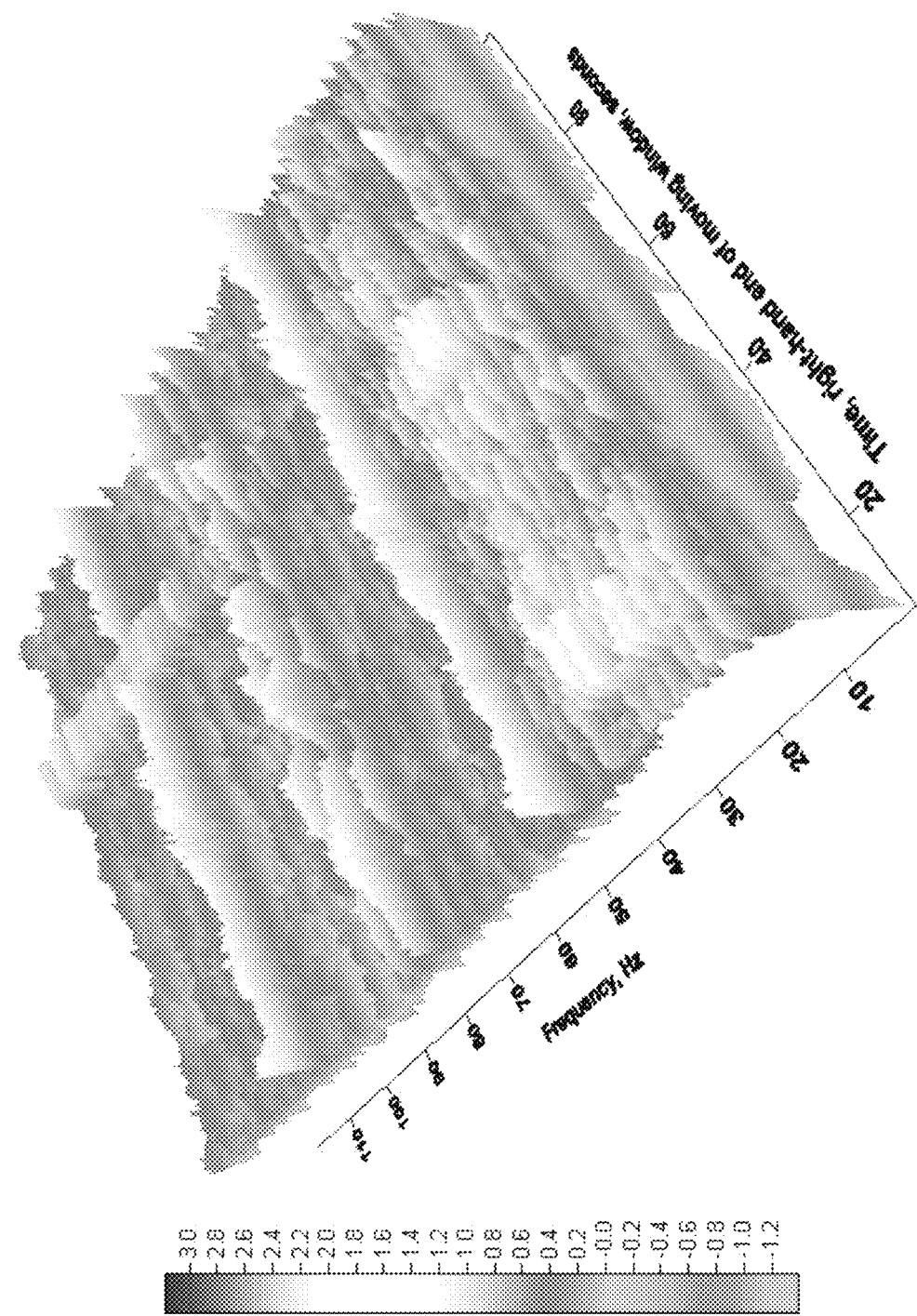
Figure 29:
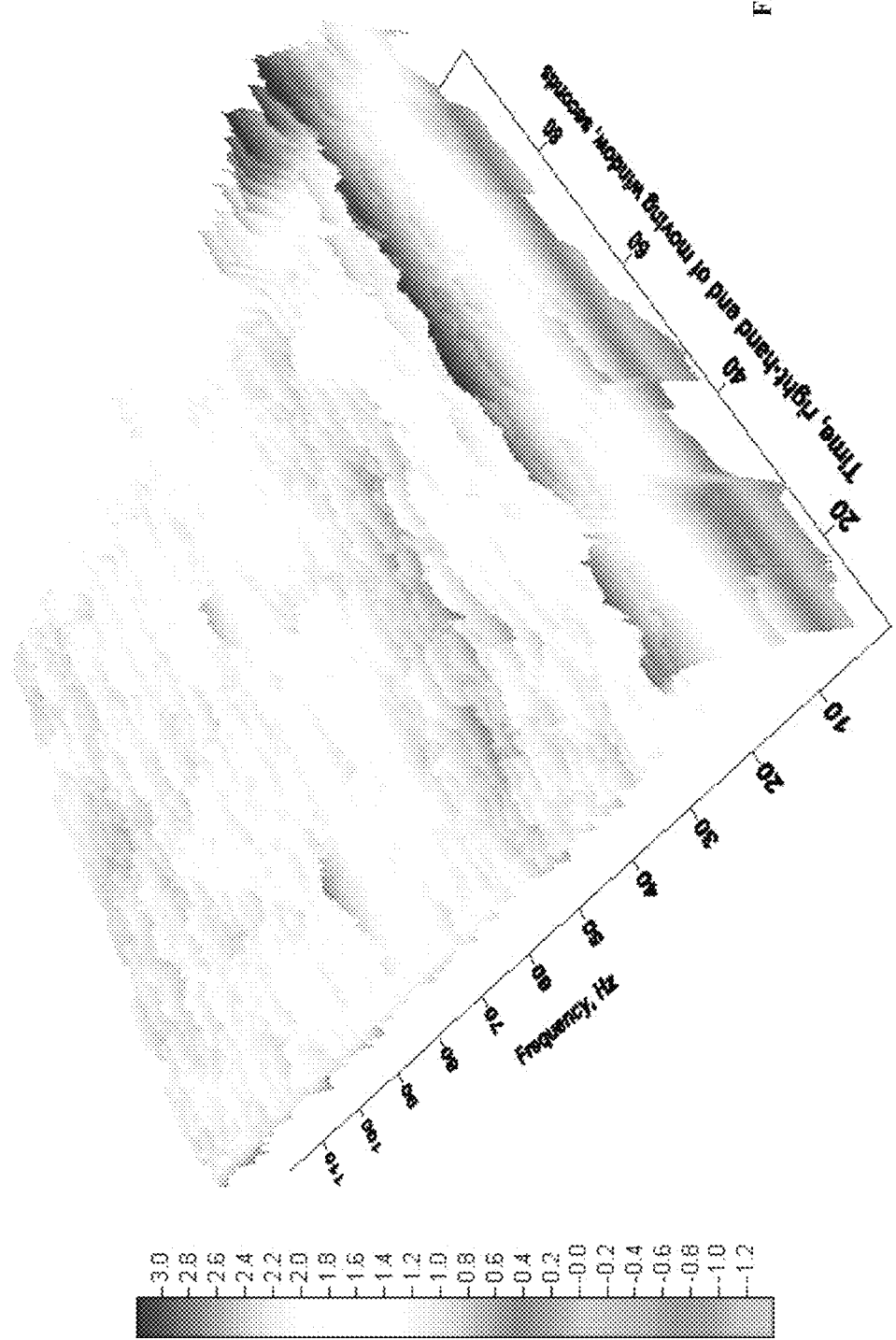
Figure 30:
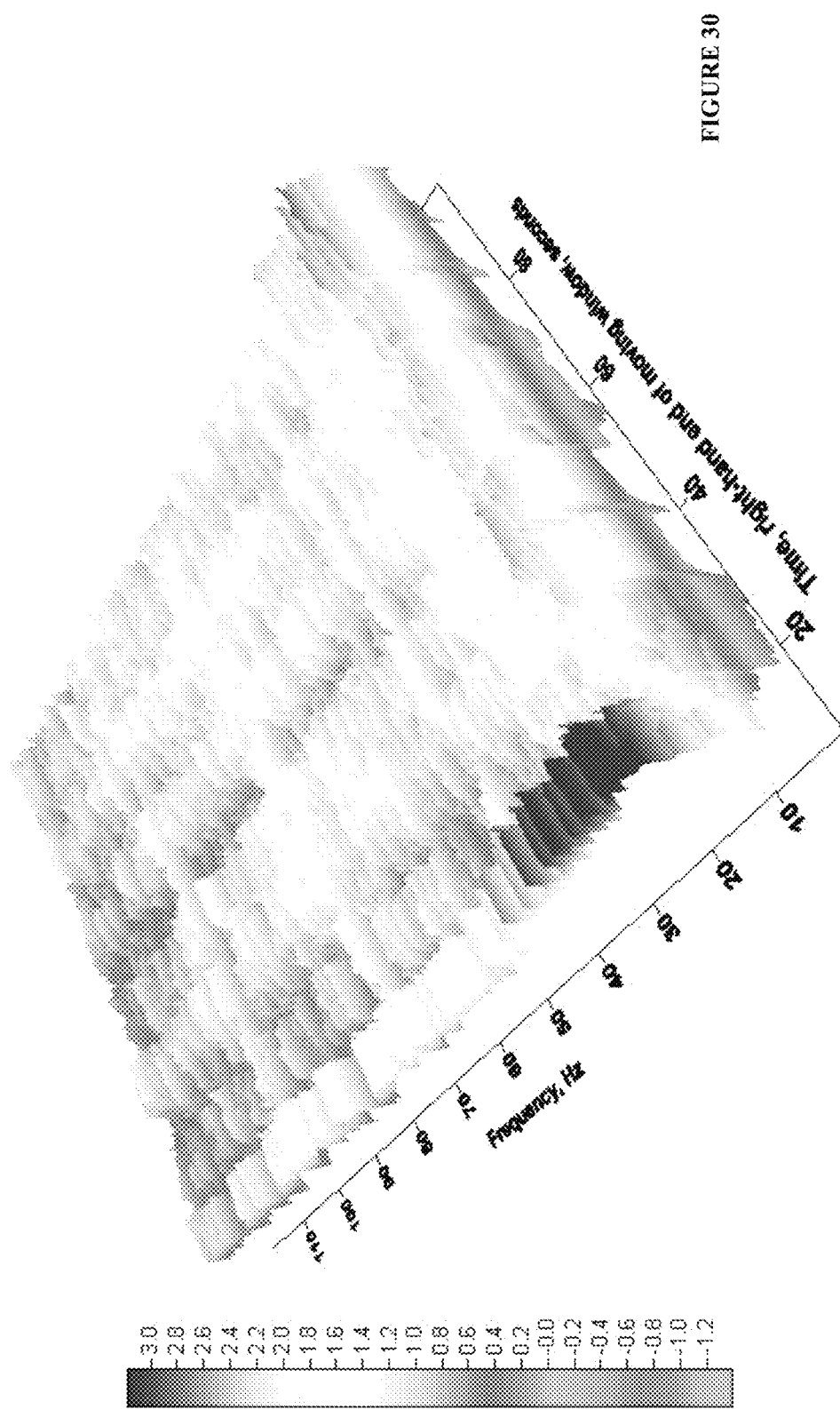
Figure 31:
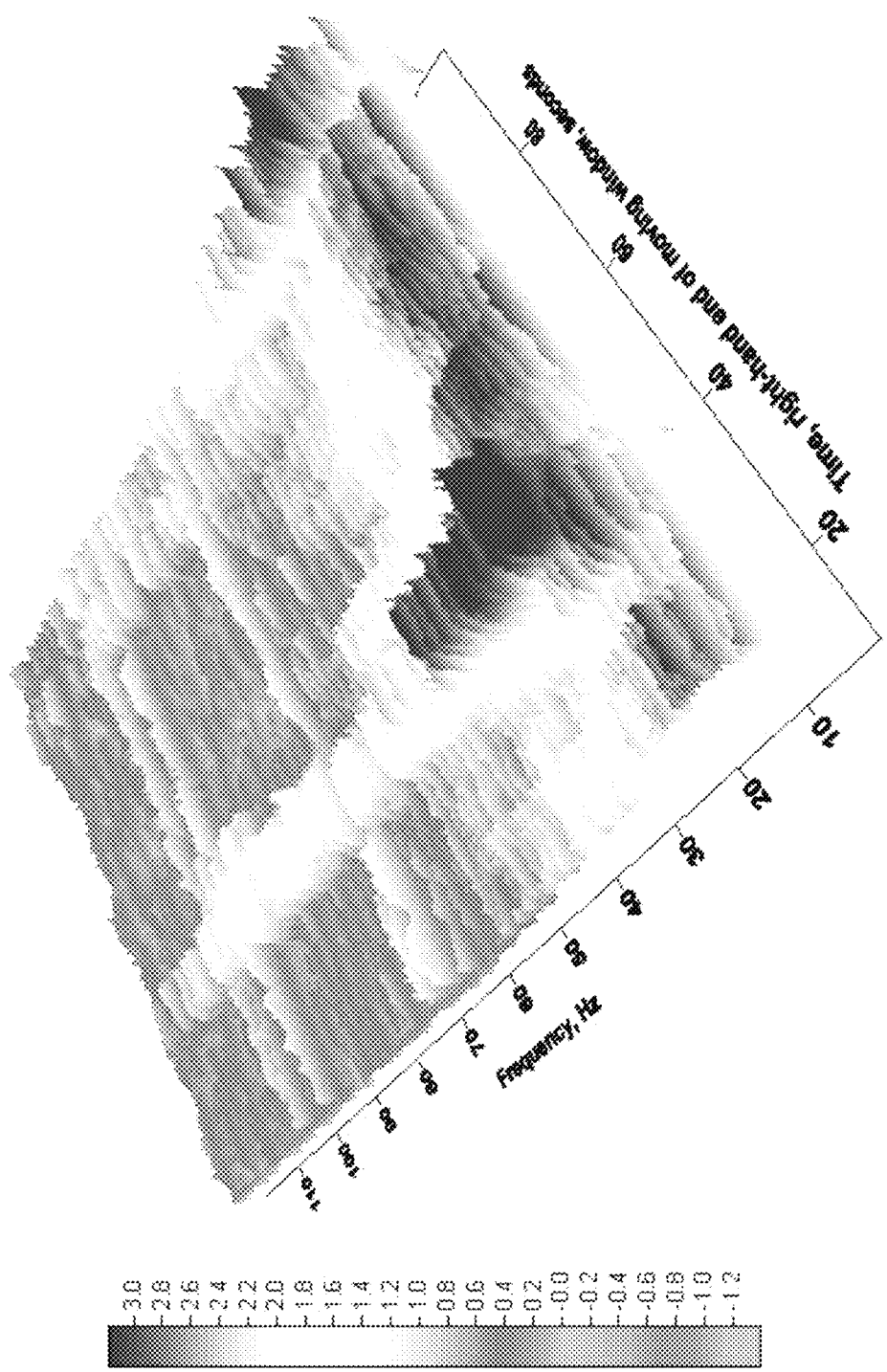
Figure 32:
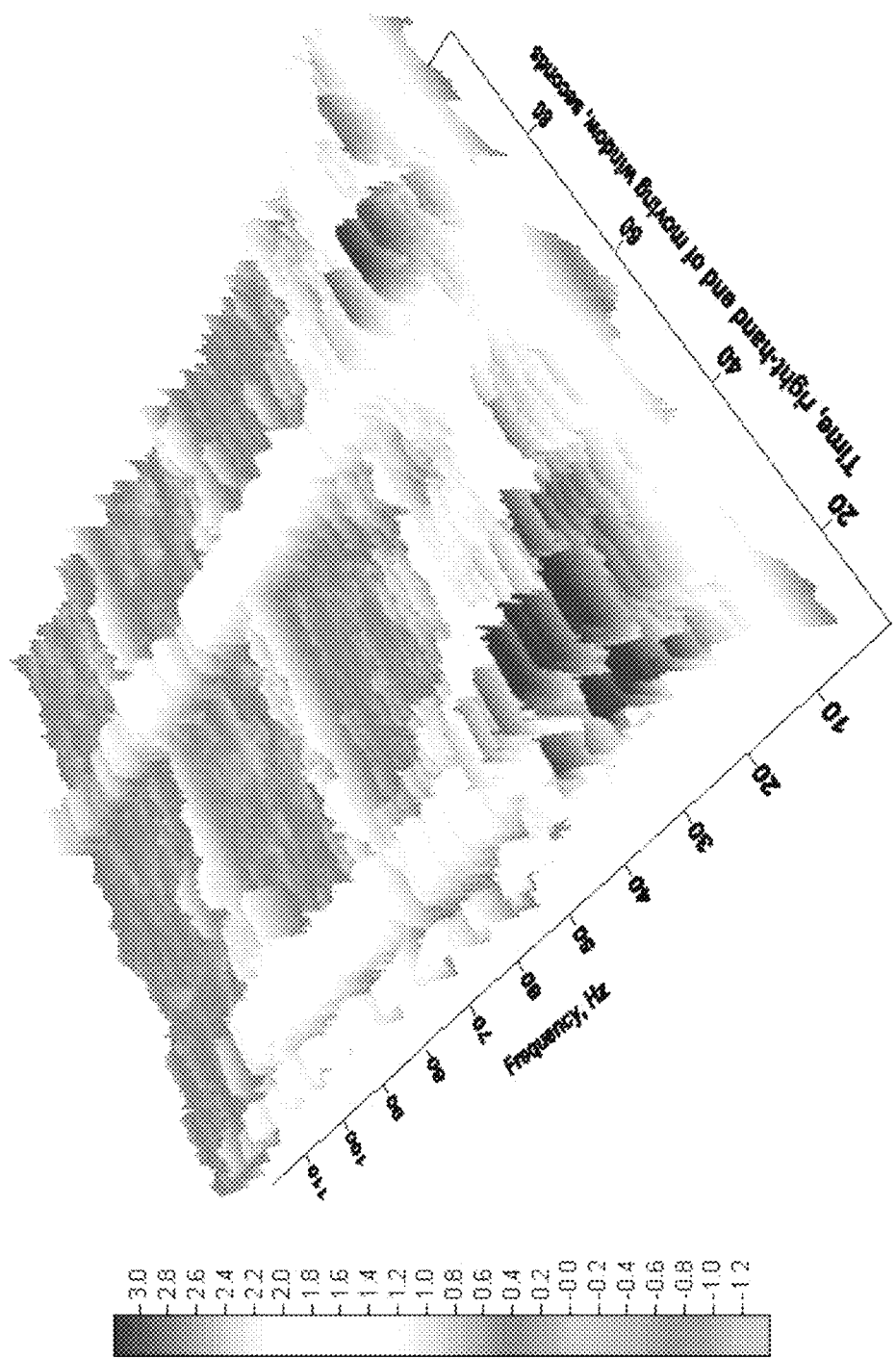
Figure 33:
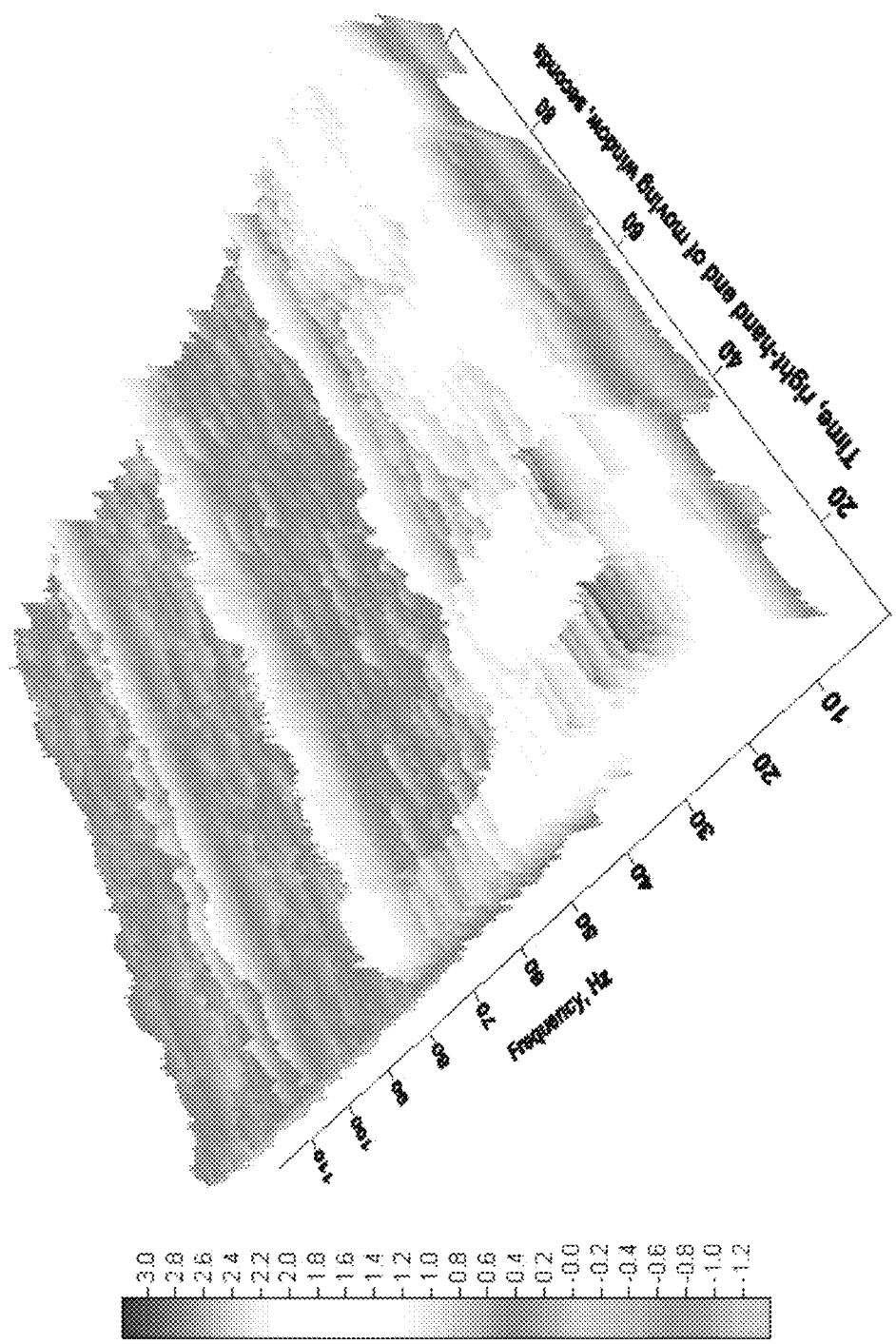

Related U.S. Application Data continuation of application No. 14/034,292, filed on Sep. 23, 2013, now Pat. No. 9,656,075, which is a division of application No. 12/729,093, filed on Mar. 22, 2010, now Pat. No. 8,560,073.

(60) Provisional application No. 61/210,850, filed on Mar. 23, 2009.

(51) Int. Cl.
*A61B 5/00* (2006.01)
*A61N 1/05* (2006.01)
*A61N 1/362* (2006.01)

(52) U.S. Cl.
CPC ........ *A61B 5/4848* (2013.01); *A61N 1/36114* (2013.01); *A61N 1/36139* (2013.01); *A61N 1/36146* (2013.01); *A61N 1/0529* (2013.01); *A61N 1/3621* (2013.01)

(58) Field of Classification Search
CPC .. A61N 1/3621; A61B 5/4094; A61B 5/0476; A61B 5/4848
See application file for complete search history.

(56) References Cited

U.S. PATENT DOCUMENTS

| | | | | |
|---|---|---|---|---|
| 2006/0111644 A1* | 5/2006 | Guttag | ................ | A61B 5/7207 600/544 |
| 2007/0213784 A1* | 9/2007 | Pless | ................ | A61N 1/36082 607/45 |

* cited by examiner

Evolution of decimal logarithm of standard deviation of EEG increments within adjacent time windows of the length 1 second. Each individual has its own pattern of standard deviation evolution. Red vertical lines – clinical onset times, blue vertical lines – expert visually scored seizures end times.

Evolution of generalized Hurst exponent values $a^*$ estimated for EEG increments within moving time window of the length 4 seconds taken with mutual shift 2 seconds.

Evolution of singularity spectra support width values $\Delta\alpha$ estimated for EEG increments within moving time window of the length 4 seconds taken with mutual shift 2 seconds. Each individual has its own pattern of $\Delta\alpha$ evolution.

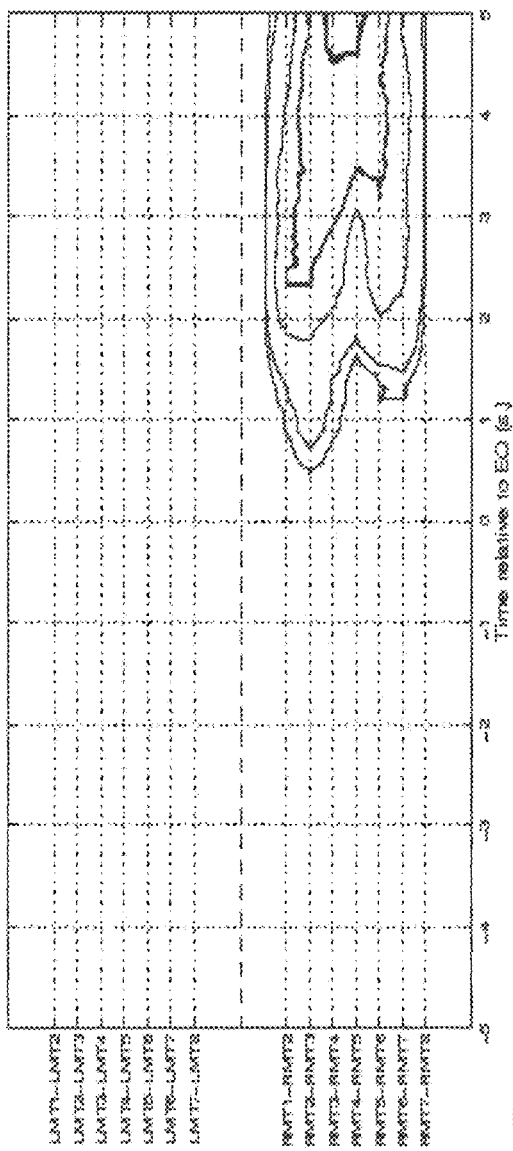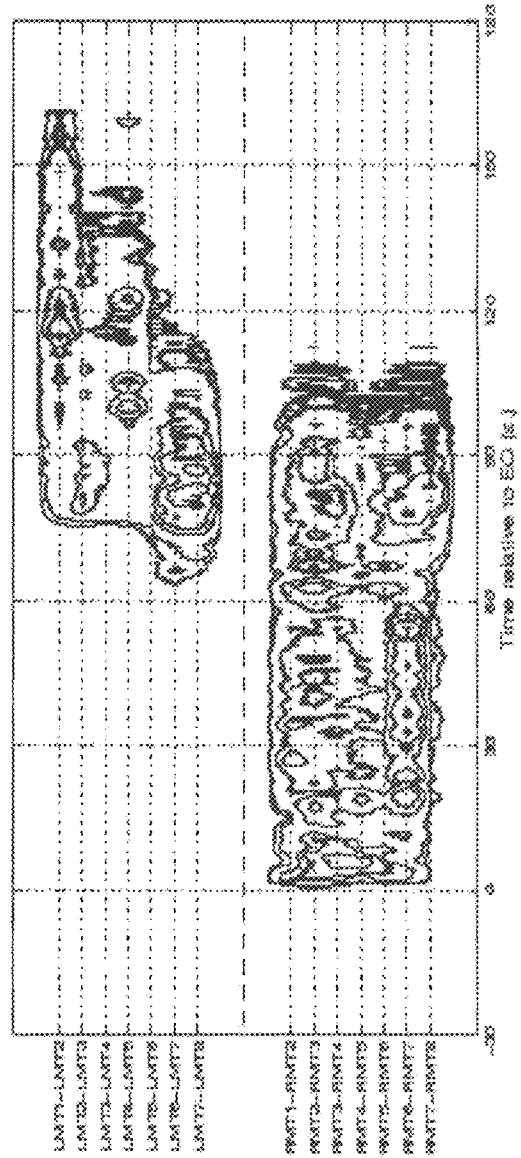
FIGURE 35

FIGURE 37(a)-(c)

SYSTEM AND APPARATUS FOR AUTOMATED QUANTITATIVE ASSESSMENT, OPTIMIZATION AND LOGGING OF THE EFFECTS OF A THERAPY

CROSS-REFERENCE TO RELATED APPLICATIONS

This application claims priority to and is a continuation application of U.S. patent application Ser. No. 15/586,433 filed on May 4, 2017, entitled "SYSTEM AND APPARATUS FOR AUTOMATED QUANTITATIVE ASSESSMENT, OPTIMIZATION AND LOGGING OF THE EFFECTS OF A THERAPY", which claims priority to and is a continuation application of U.S. patent application Ser. No. 14/034,292 filed on Sep. 23, 2013 (now U.S. Pat. No. 9,656,075), entitled "SYSTEM AND APPARATUS FOR AUTOMATED QUANTITATIVE ASSESSMENT, OPTIMIZATION AND LOGGING OF THE EFFECTS OF A THERAPY", which claims priority to and is a divisional application of U.S. patent application Ser. No. 12/729,093 filed on Mar. 22, 2010 (now U.S. Pat. No. 8,560,073), entitled "SYSTEM AND APPARATUS FOR AUTOMATED QUANTITATIVE ASSESSMENT, OPTIMIZATION AND LOGGING OF THE EFFECTS OF A THERAPY", which claims priority to Provisional Application No. 61/210,850, filed on Mar. 23, 2009 which are all incorporated in their entireties by reference.

Safe and effective therapies for pharmaco-resistant seizures are a major unmet medical need affecting approximately 36% of all epileptics (~1.1 million in the US and ~18 million worldwide). These subjects have poor quality of life, the large majority are unemployed, suffer from depression and are 40 times more likely to die suddenly than age-matched subjects in the general population. Brain electrical stimulation, either directly or indirectly (vagus nerve stimulation), and contingent (triggered by the onset of seizures) or non-contingent (e.g., periodic, round-the-clock), and other therapies such as localized cooling of the epileptogenic zone or direct delivery of drugs to it, hold great promise for these patients. However, in light of the results of large recent clinical trials showing a modest mean decrease in seizure frequency of 40-60% on patients than remain on multiple anti-seizure drugs, optimization is required if they are meet efficaciously and cost-effectively this medical need. This invention addresses in a novel, effective, and systematic manner, the complex and demanding task of optimization of interventional brain therapies for control of undesirable changes of state. In its preferred embodiment this invention addresses brain state changes and in particular epileptic seizures. Therapies for other neurological (e.g., pain, movement), psychiatric (e.g., mood; obsessive compulsive), and cardiac (e.g., arrhythmias) disorders may be optimized using the approaches described herein.

Epileptic seizures occur with or without discernible or visible clinical manifestations.

In the case of seizures originating from discrete brain regions (known as partial or "focal" seizures) the electrical abnormalities usually precede the first clinical manifestation (subjective or objective) and in a large number of these patients, impairment or loss of responsiveness occurs some time after the first clinical manifestation. Also, if the seizure becomes secondarily generalized, loss of consciousness (to be distinguished from loss of responsiveness) occurs after loss of responsiveness. Commonly, abnormal electrical activity outlasts the loss of consciousness and consciousness is regained before responsiveness returns to normal (for the patient) levels. In certain epileptic brains the transition from the non-seizure to the seizure state may be gradual, providing a window for prediction and intervention before the transition is complete. Degree of responsiveness may be tested and quantified in real-time using a wide variety of available tests.

Therapy for control of disorders such as epilepsy which manifest intermittently, aperiodically and briefly (ranging from seconds to rarely >2 min) and are classified as dynamic, meaning that state changes (from normal to abnormal and vice-versa) are caused by changes in the system's control parameter(s) are specially challenging. To increase the probability of therapeutic success local, global, structural, dynamical, and state factors influencing the state change, must be identified and measured with useful precision and at informative time scales. These concepts and considerations required to formulate treatment and optimization strategies are lacking in the state-of-the art therapies.

While this invention is aimed at optimizing a therapy, nothing in its specification precludes delivery of a therapy prior to optimization or without optimization. Indeed, optimization cannot take place if a therapy has not been administered and its effects (beneficial and detrimental) quantified. If a therapy cannot be optimized (in terms of increasing its beneficial effects), optimization may be effected by decreasing the number or intensity and duration of its adverse events. Adverse effects include but are not limited to increase in seizure frequency or severity, cognitive impairment in functions such as memory, language, mood (depression or mania), psychosis. These adverse effects may be quantified using cognitive, electrical, thermal, optical and other signals and logged to computer memory. In the case of signals that lack easily detectable or recognizable electrical or other correlates, they may be characterized using a semi-quantitative approach such as psychiatric scales, caregiver observations or patient diaries.

The term "therapy" may be interchangeably used with the term control for which a theory exists (Control Theory) in the field of engineering. Since therapy and control share the same aim, it is appropriate to adopt certain concepts form this theory as well as from the fields of dynamics to generate a rational approach and strategy for the management of pharmaco-resistant seizures.

The epileptic brain may be conceptualized as a non-stationary, non-linear, "noisy" system that undergoes sudden unexplained reversible transitions from the non-seizure state. The manner in which this transition occurs may be "gradual" (through a process of "attractor deformation") or sudden (through a "leap" from one state to another) as observed in bi-stable or multi-stable systems. Dynamical theory teaches that a system may be defined by its dimension (which corresponds to the minimum number of variables required to specify it). The identification of a system's dimension greatly benefits from the identification of a spatio-temporal scale of observation that corresponds to a representative sample of the system (so-called mesoscopic scale), thus obviating the need to study the whole system at all scales, a daunting and impracticable task in the case of the mammalian brain. The epileptic brain's dimensionality and its mesoscopic scale have not been effectively specified to date. This knowledge void forces the treatment of the brain as a "black-box".

While by definition a "black-box" is not amenable to direct inquiry, it can be indirectly studied through perturbations of system inputs. A known, well characterized input is "fed" into the "black-box" and the output is carefully recorded and characterized quantitatively or qualitatively and compared to the input. Transformations, if any to the input properties provide indirect but useful information about the "black-box" that may be captured mathematically as transfer functions. For example, if doubling the amplitude of the input translates into doubling of the output, the system is considered linear. However if doubling the input causes an exponential increase in the output, the system is non-linear (likely the brain's case). If sine waves are fed into the black box and 60 Hz. activity appear on them as they exit the box, it is reasonable to infer that the box corrupts the waves and is "noisy". Successful control of the behavior of "black-boxes" cannot occur if the measurements of its output are not representative of the state(s) and site(s) from where they are obtained, reasonably precise and also reproducible from measurement to measurement.

Global and local factors (many state-dependent) also shape the response to therapies. For example, the rate and direction of diffusion of particles and molecules in animal tissue (e.g. brain), depends on multiple factors including size, chemical valence and the size and tortuosity of the extracellular space. In certain tissues, such as the brain's, the average values of the dielectric constant, or permittivity, and of the resistance are not equal at all points of the volume which the particles and molecules occupy. This anisotropy, which varies by a factor of 5-10 between two orthogonally-selected directions, such as between the vertical (or radial) and horizontal (or transverse) directions in a brain's cortex or its axons, ensures that diffusion of endogenous and exogenous (e.g., electrical stimulation) currents is not homogenous. This lack of homogeneity (and of isotropy) in the case of a therapy (e.g., electrical stimulation) that must diffuse through the tissue to exert its beneficial action is likely to decrease efficacy, a feature that must be considered for control and optimization purposes.

The diffusions of electrical currents within the brain, which as vectors have both magnitude (potential) and direction, are the result of electrostatic forces caused by the transient accumulation of charges and also of electrodynamic actions arising from ionic or electronic currents in the volume which surrounds the local accumulations of such charges. Intracortical diffusion of electrical charges (ions) and currents, takes place at several spatial domains or scales (active membrane sites, cells, columns and the cortical synergic groups where they flow differentially through the lattice of intercellular spaces and through the network of glial cells. These flows occur through a large number of routes at their disposal, each route being the path for only a small part of the total current (Kirchhoff's law), a "fractionation" that may result in insufficient (or excessive) current densities and low or no efficacy or adverse effects in certain sites.

An additional challenge to controlling brain state changes is that tissue anisotropy is not uniform or constant but it varies as a function of differences in cortical cytoarchitecture and of the state of activation within the volume where putative (endogenous) or exogenous (e.g., electrical stimulation) currents diffuse. These inter-regional or areal differences translate into time- and space-constant differences that make the probability of generation of action potentials and their conduction velocities behave differentially. When present, these differences lead to the spatio-temporal dispersion of endogenous or exogenous (e.g., electrical stimulation) currents and to a lower than desirable current flux through the region of interest—and thus potentially to loss of therapeutic efficacy. However, the opposite may also occur and current flux may be higher than desirable for efficacious control or safety purposes. The fact that electrical currents both trigger and control seizures depending on the stimulation parameters used, such as frequency and intensity, among many other factors, should not be ignored by those who use this modality for therapeutic purposes. In addition to the inherent widespread morphological or structural anisotropy of nervous tissue, diffusion of electrical potentials also depend on: a) the state (at both global and local levels and at long and short time scales) of the network; b) on the level (spike frequency) and pattern of spike activity and the "valence" (inhibitory or excitatory) of inputs and outputs or efferences, which are likely reflected in changes in tissue conductivity/diffusivity and responsivity to both endogenous and exogenous currents. For example, tissue resistivity is altered by bursts of epileptiform discharges of only a few seconds duration and frequent seizures often alter tissue osmolality, both of which are likely to negatively impact therapeutic efficacy, unless these factors are taken into account and measured.

As for electrical stimulation, the most investigated therapeutic modality for pharmaco-resistant epilepsies, the electric field E, at every point i on the surface of a charged needle (which closely approximates in shape the electrodes used in humans for treatment purposes) is similar to the set of diffusion limited aggregation growth probabilities and in this sense, the electric field E, is also a multi-fractal set. This means that different "regions" in the electric field (and by extension in the tissue where the field is active) are not only fractal but have different fractal values or properties at different points. That an electric field as described above is a multi-fractal set brings to the fore one of the central themes of this work, the spatio-temporal "inhomogeneity" of a therapy (electrical) and the requirement (for optimization of this treatment modality) to apply concepts (from multi-fractal theory, among others) to quantitatively characterize this complex phenomenon.

Prior art therapies also ignore the dampening and the linear and non-linear distortions of frequency, phase, harmonics and amplitude that invariably occur as currents travel through brain tissue. More specifically, prior art therapies and interventions for blocking, abating, or preventing undesirable state changes ignore tissue anisotropy, dielectric hysteresis, state and circadian influences at local and global scales and the changing nature (non-stationarity) in the type, pattern and level of neuronal activity as a function of state and time as reflected in intra-individual and inter-individual differences in seizures.

The present inventor has investigated the foregoing issues in conducting research to improve therapies available to epileptic patients. FIGS. 1-33 depict the power spectrum (a representative estimation of brain activity) of neuronal activity recorded over 162 hours from the same site in the same human subjects. These figures demonstrate how the activity of the epileptogenic zone as reflected in the power spectrum changes as a function of time. A look at these spectrograms and at the temporal evolution of the values of a) the decimal logarithm of the standard deviation (FIG. 34(a)); b) of the generalized Hurst exponent (FIG. 34(b)) and of the singularity spectra width values (FIG. 34(c)) of two seizures recorded from 11 subjects (each subject's seizures are in the same row), point clearly to the importance of tailoring therapy to intra- and inter-individual differences; it is improbable that electrical stimulation with fixed parameters (the current state-of the-art) delivered to each of these seizures will have the same effect, let alone that it will be uniformly beneficial.

The inhomogeneity/lacunarity of involvement of tissue during an undesirable event (see contour plots of FIG. 35; upper panel: seizure onset right temporal lobe shown at high temporal resolution; lower panel shows the spatio-temporal evolution of the seizure over both temporal lobes at low temporal resolution) underscores the importance of quantifying and accounting for lack of uniform tissue involvement (inhomogeneity) by these abnormal events.

If seizure properties features are determined using spectral methods and classified into clusters (each cluster represents a given type of seizure) using vectors of their properties (e.g., the log of the standard deviation, the singularity spectra width values, etc.), the present worker have found that there is more than one cluster or seizure type for each subject, for seizures originating from the same site, and that the number of clusters changes in time, suggesting corresponding changes in the number of main "modes" of neural activity.

Figure 36:
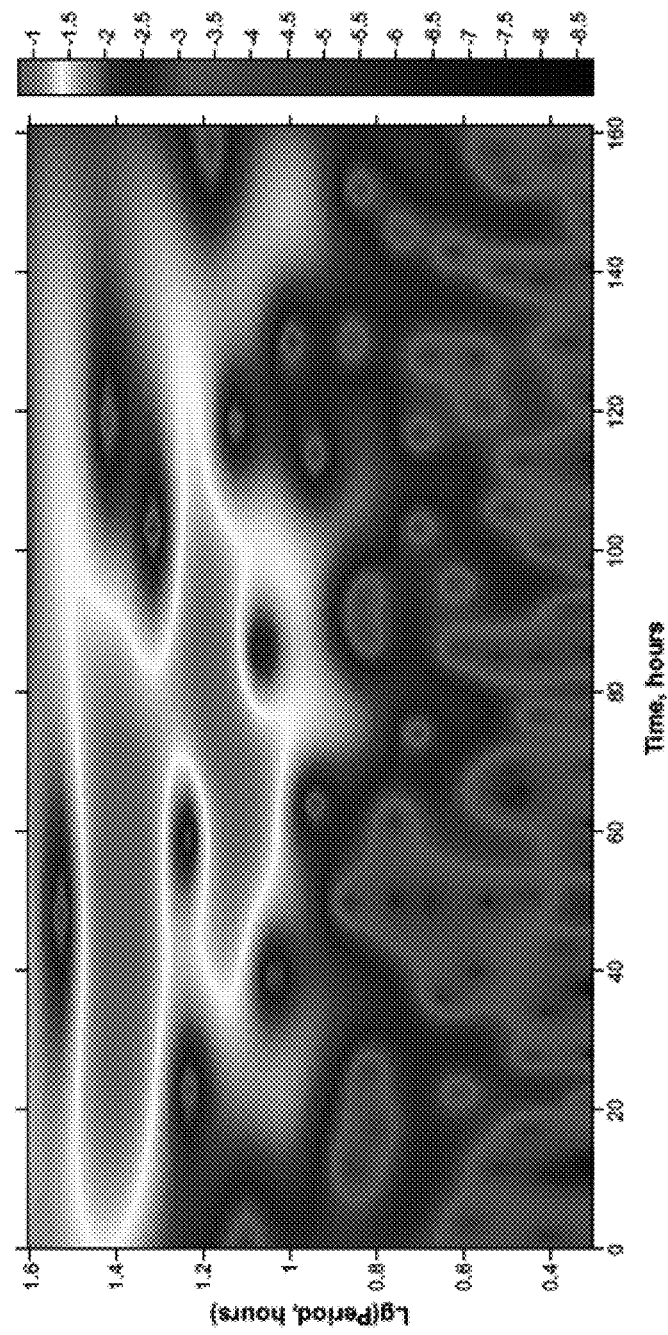

Seizures may have a latent circadian periodicity which could be extracted as periodicity in the variation of the pseudo-F-statistic maximum values. This periodicity may disappear as a function of time, state and other factors. FIG. 36 depicts the time evolution of the values of the Pseudo-F statistic (a measure of cluster tightness) of seizures recorded from the same site and from the same individual. Notice the red clouds seen at 1.2 (~12 hr) and 1.4 (~24 hr) in the y-axis (the y-axis is the log of time) and present from the start of the recording and indicative of a circadian tendency for seizure properties to cluster, that is, to be highly similar, vanishes after approximately 110 hours (x-axis, time in hours) indicating the loss of the circadian trend. This observation further exposes the variability of abnormal brain activity over intermediate time scales (tens of hours), variability that must be detected and measured to optimize (as a function of time) therapeutic efficacy.

Other important factors that are ignored by current therapies are: (i) seizure blockage does not necessarily translate into prevention of loss of cognitive functions, the most disabling seizure symptom; (ii) the inherent and inevitable delay (vide supra) in arrival of the therapy to its target site, delay which depends among others on the therapeutic modality (relatively short for electrical currents and relatively long for drugs and thermal energy); (iii) the degree (low or high) of morphological similarity or rhythmicity among waves that make up a seizure, determines the probability (high if the waves are highly similar) of blockage especially if electrical stimulation is the therapy of choice; (iv) the lack of uniformity in flow direction and in density of both the abnormal activity and the therapy, as well the differences in their speed of propagation, their synchronization levels and degree of rhythmicity.

SUMMARY OF THE INVENTION

In one embodiment, the present invention provides a method for assessment, optimization and logging of the effects of a therapy for a medical condition. In one embodiment, the method comprises:

(a) receiving into a signal processor input signals indicative of the subject's brain activity;

(b) characterizing the spatio-temporal behavior of the brain activity using the signals;

(c) delivering a therapy to a target tissue of the subject;

(d) characterizing the spatio-temporal effect of the therapy on the brain activity;

(e) in response to the characterizing, optimizing at least one parameter of the therapy if the brain activity has not been satisfactorily modified and/or has been adversely modified by the therapy;

(f) characterizing the spatio-temporal effect of the at least one optimized parameter; and (g) logging to memory the at least one optimized parameter.

The present invention also provides a method for optimizing the effect of a therapy. In one embodiment, the method comprises determining a wave rhythmicity of brain activity of a subject, and applying a therapy to a target tissue of the subject at a first time, wherein the target tissue and the first time are based upon the wave rhythmicity.

The present invention also provides a method for optimizing the effect of a therapy. In one embodiment, the method comprises estimating the level of synchrony within one brain epileptogenic region, and determining if the level of synchrony is above or below a value associated with a high probability of blockage of an epileptic event when the therapy is applied. In a further embodiment, delivery of the therapy is timed to coincide with the synchrony level reaching the value associated with the high probability of blockage of the epileptic event.

The present invention also provides a computer readable program storage unit encoded with instructions that, when executed by a computer, perform a method as described above and herein.

BRIEF DESCRIPTION OF THE DRAWING FIGURES

FIGS. 1-33 show three-dimensional power spectra of short ECoG segments from the same subject and from the same brain site, but at different times of days, illustrating the changes in power at different bands as a function of time, state, etc. This suggests non-stationarity of the system, a phenomenon that state of the art therapies fail address and which this invention addresses.

Figure 34A:
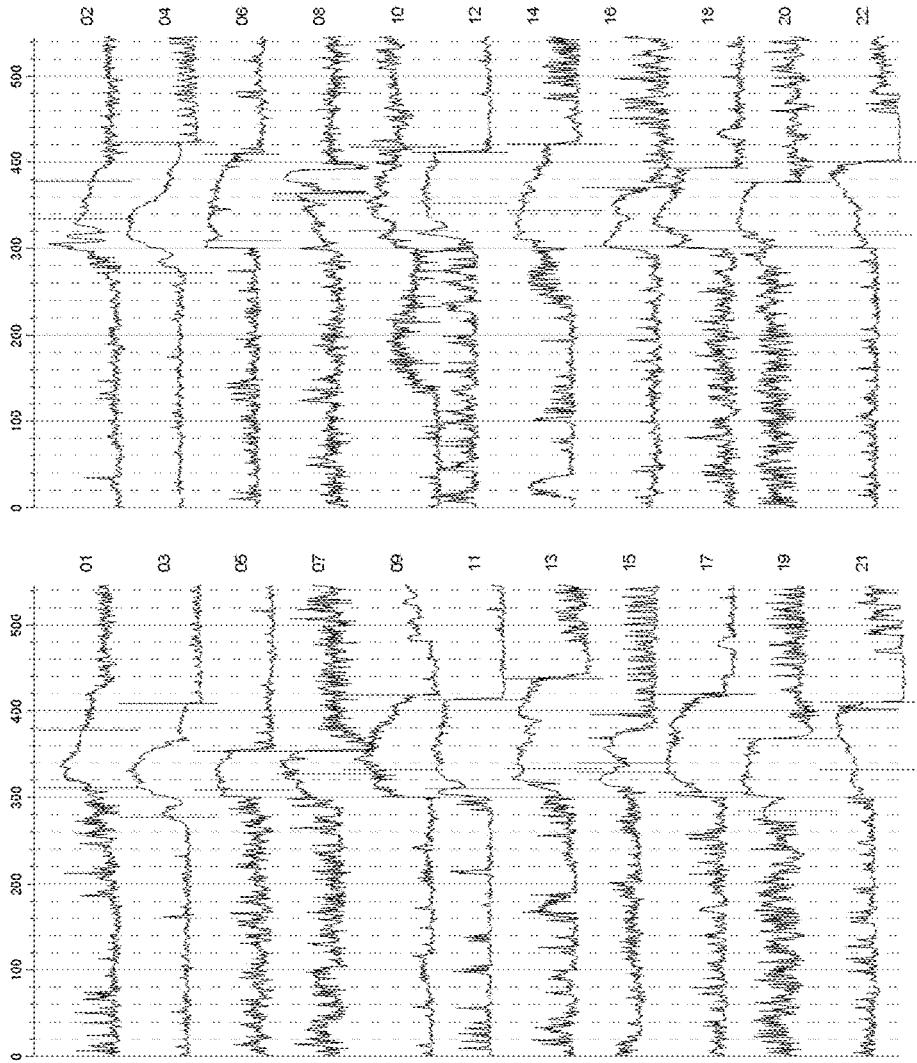
Figure 34B:
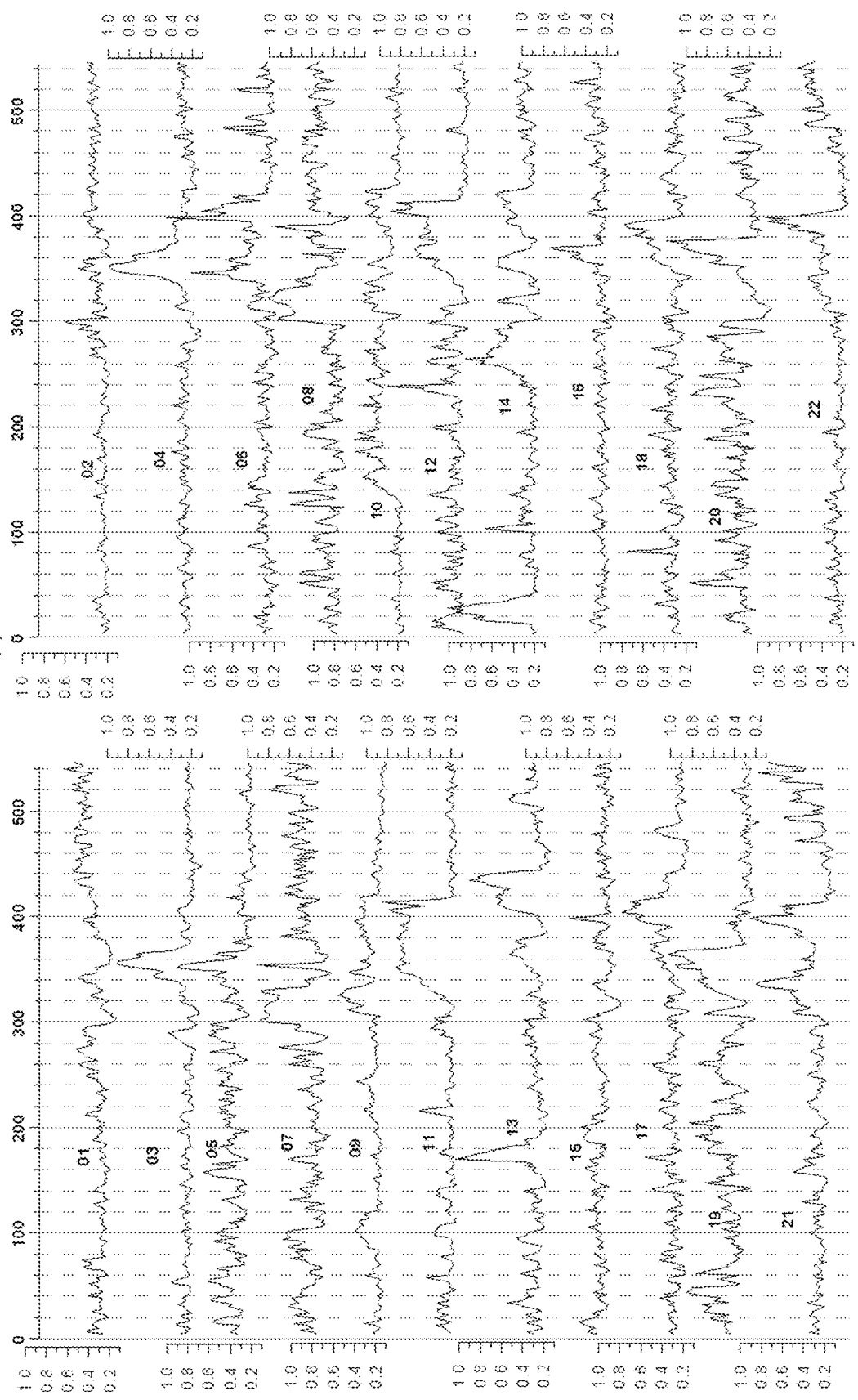
Figure 34C:
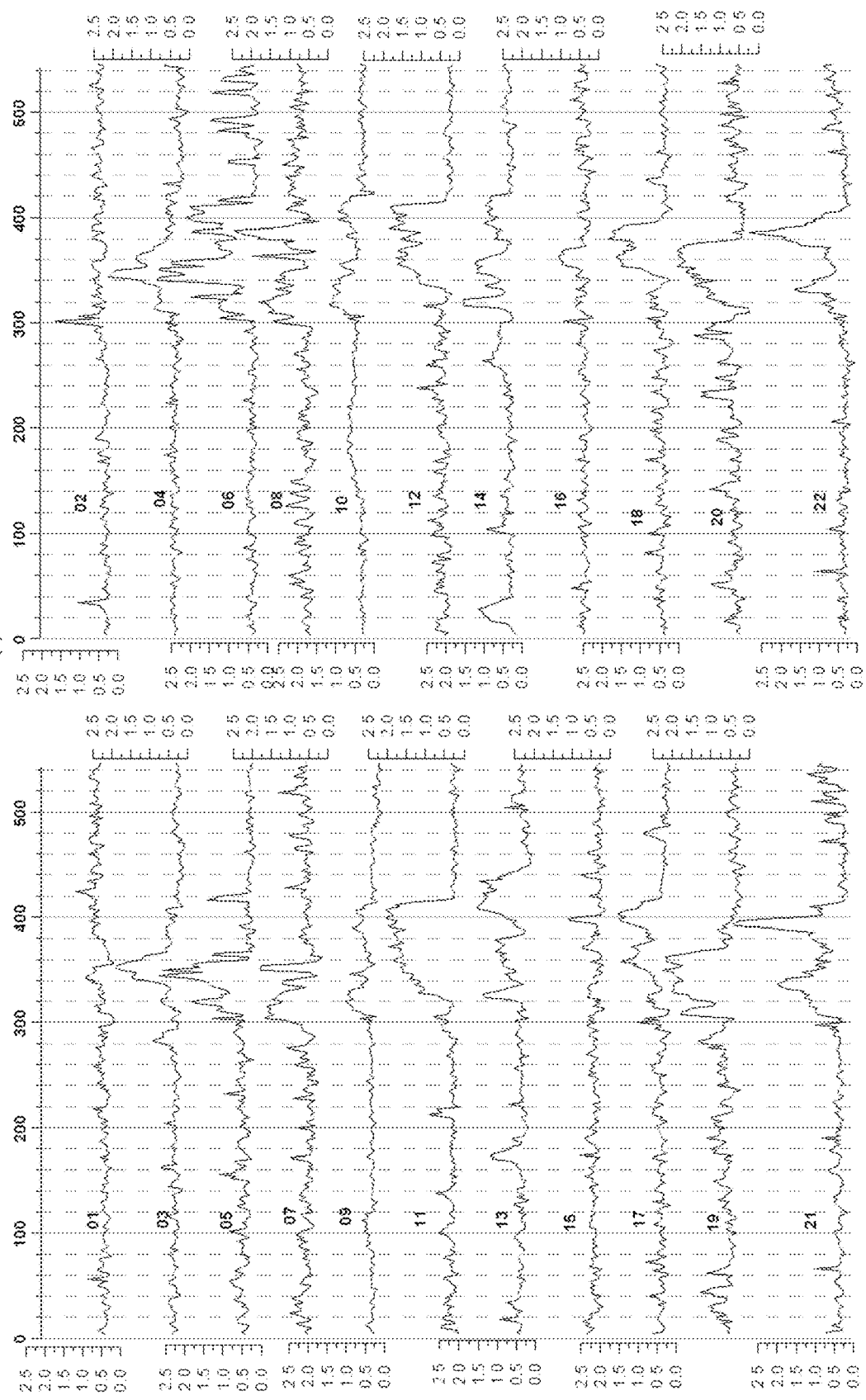

FIGS. 34(a), 34(b), and 34(c) show the evolution of the decimal logarithm (FIG. 34(a)), generalized Hurst exponents (FIG. 34(b)), and singularity spectra (FIG. 34(c)) of seizures (two seizures/subject) of EEG increments recorded from eleven subjects with pharmaco-resistant epilepsy. FIG. 34(a) shows an evolution of decimal logarithm of standard deviation of EEG increments within adjacent time windows of the length 1 second. Each individual has its own pattern of standard deviation evolution. Red vertical lines—clinical onset times, blue vertical lines—expert visually scored seizures end times. Each row has two seizures recorded from the same subject and from the same brain site. Notice intra- and inter-individual differences, that underscore the importance of tracking as a function of time (e.g., time of day, week, month, etc.) and of state (e.g, awake versus asleep; if awake attentive versus relaxed; if asleep in non-REM versus in REM sleep; if in non-REM in stage I versus III, etc.) their properties and using this information to adapt and optimize therapy, both on a seizure-by seizure- and on individual bases.

FIG. 35 shows contour plots of a single seizure. Notice spatial power spectral differences over area of seizure origin (epileptogenic zone), which differences are indicative of inhomogeneity. Not shown are the differences in the temporal evolution of this abnormal activity at the different sites, another type of inhomogeneity. Therapeutic efficacy may depend on the ability to tailor time of delivery, intensity/dose, type of therapy, location, geometric configuration and number of therapy sources to the spatio-temporal characteristics and the evolution of the undesirable event.

FIG. 36 shows the decimal logarithm of the squared Morlet wavelet coefficient for the maximal Pseudostatistic F variation, in reference to the clustering of seizures recorded from a subject (same brain site) over approximately 150 hours. A strong periodic component at approximately 12 and 24 hours (see red cloud) is seen for the first 110 hours, probably reflecting circadian influences. However, notice that this periodicity, weakens considerably after 110 hours, pointing again to the non-stationarity of undesirable events (seizures in this case) and the importance of tracking the evolution of their properties over multiple temporal scales so as to optimize therapy.

FIG. 37(a) shows the effect of five cathodal monophasic (DC) pulses on six different seizures, recorded from the same site. Notice that seizures whose waves are highly similar or rhythmical (as quantified by the rhythmicity index whose value (e.g., 0.91) appears to the left of the pulse artifacts and above the waves) are abated, while those whose waves are somewhat dissimilar and have low rhythmicity are not.

FIG. 37(b) shows that even a single cathodal monophasic pulse may abolish a highly rhythmical seizure, while having no effect on one with low rhythmicity.

FIG. 37(c) shows an enlarged impulse or evoked response to monophasic cathodal stimulation of one of the seizures shown in FIG. 37(a). The impulse responses to cathodal stimulations show subtle phase shifts (phase resetting) which are predictive of a beneficial or non-beneficial response. Using available optimization search methods, the timing of delivery of a single (or very pulses) to cause the desirable (beneficial) phase may be found for each seizure.

Figure 38:
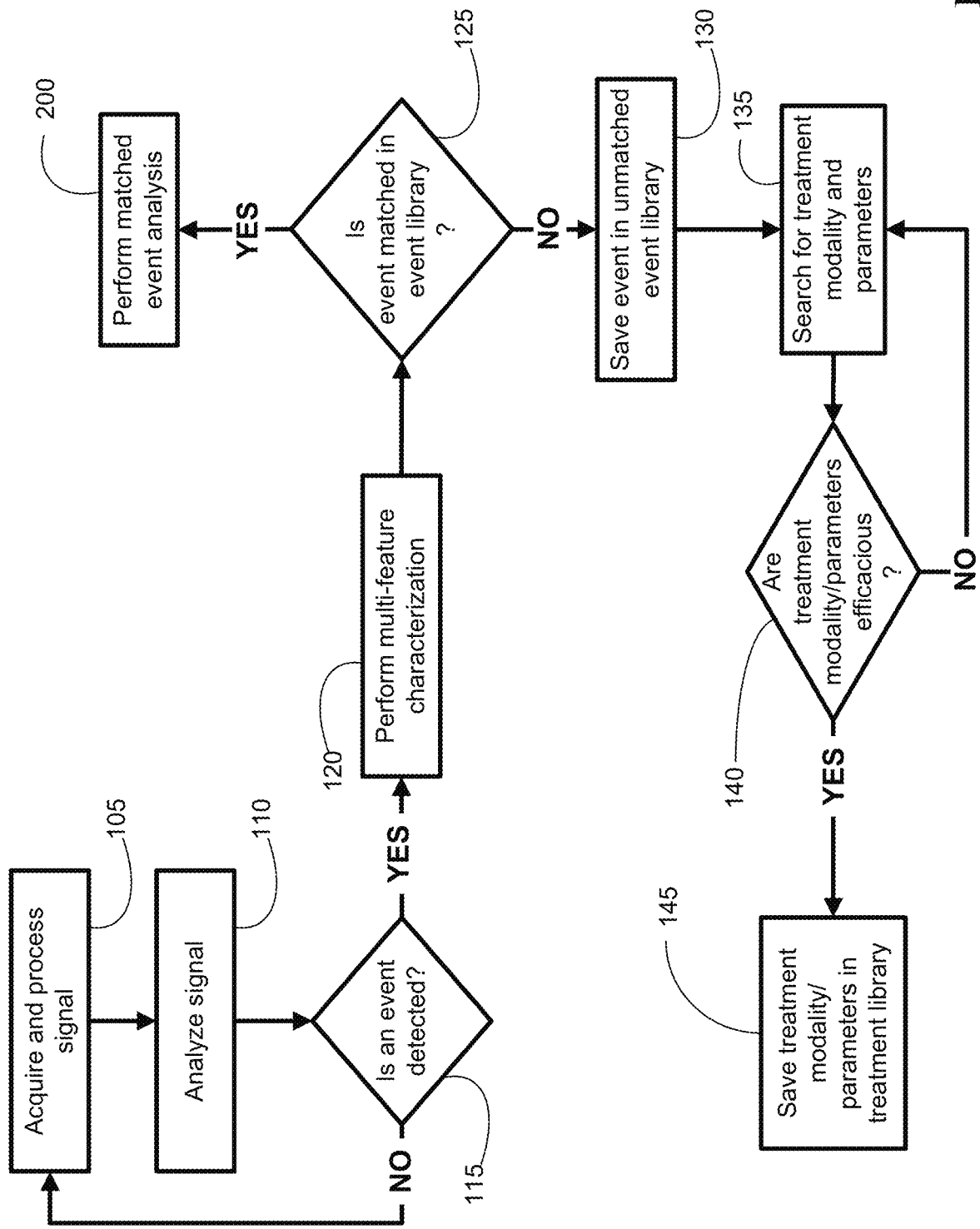
Figure 39:
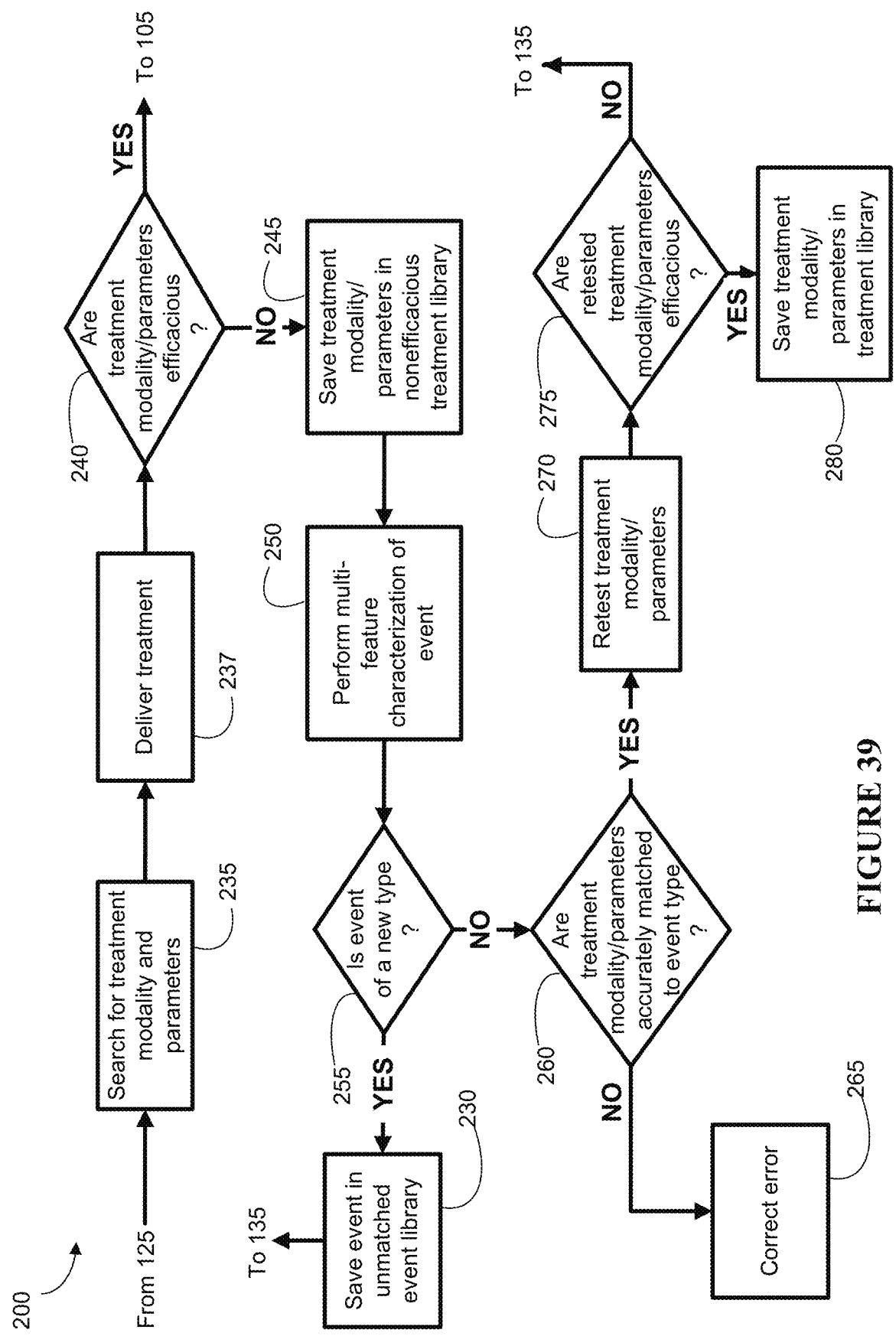

FIGS. 38-39 show a flowchart depiction of one method, in accordance with the present invention.

DETAILED DESCRIPTION OF THE INVENTION

The degree of morphological stereotypia (similarity) among waves (denoted herein as rhythmicity) that make up seizures is an indirect measure of neuronal synchronization within a region and between regions. The occurrence of trains of waves with highly similar waveforms (frequency and amplitude) within a brain region or between brain regions may be interpreted as an indication that these waves are generated by highly similar and phase-locked generators. Rhythmicity is a novel measure of waveform stereotypia and indirectly of the spatio-temporal behavior and synchronization of those waveforms' generators. Rhythmicity may be measured using the autocorrelation function (ACF) of a (possibly pre-filtered) linearly detrended signal; normalization by total signal power in the window is performed so that the ACF has a value of 1.0 at zero lag. The ACF may be written into a computer program for on-line (real-time) automated quantification and triggering of a therapy.

Figure 37:
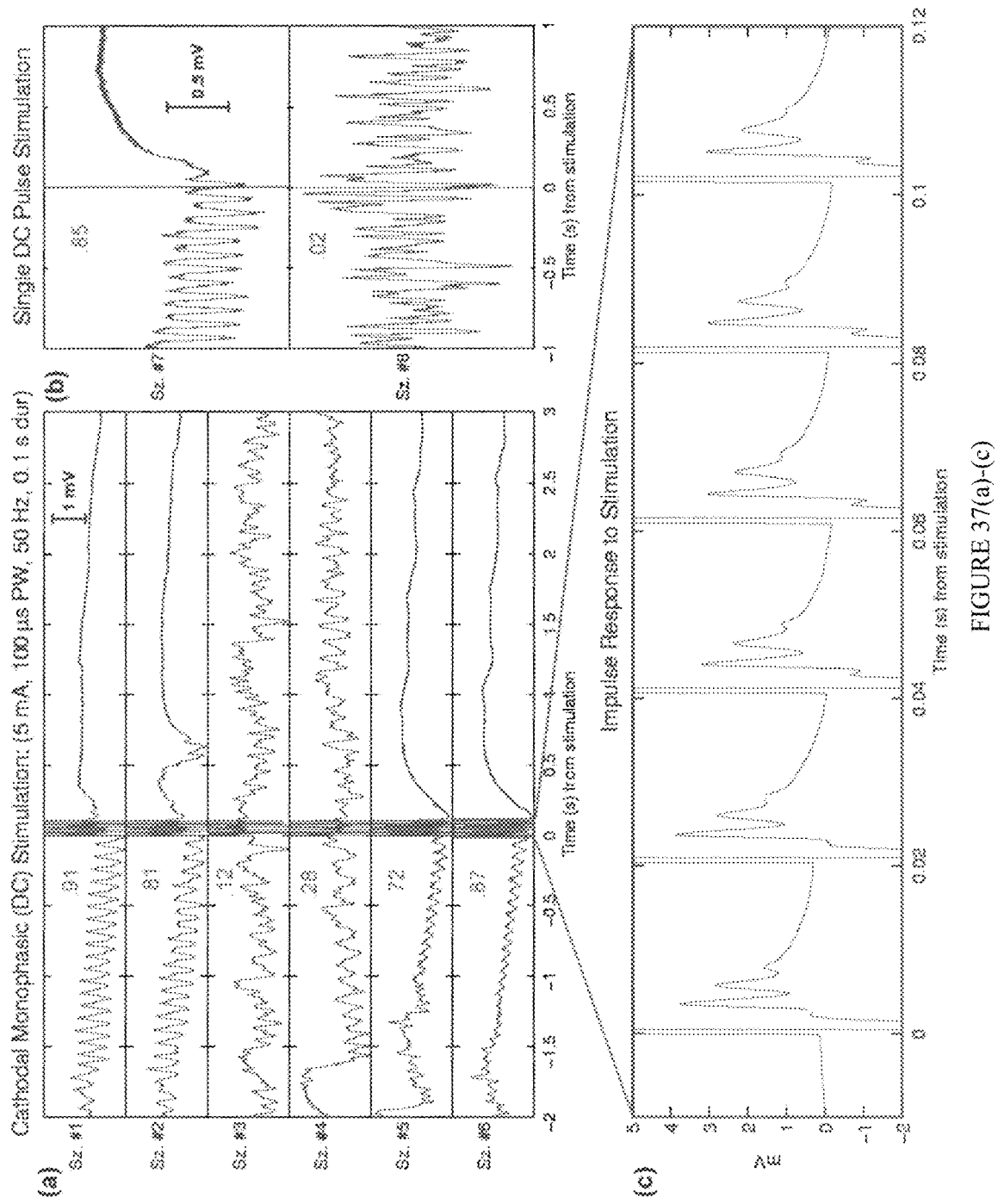

Neuronal rhythmicity for a time epoch of signal is defined as the value of the ACF at the first local maximum to the right of the first zero-uperossing. As the signal evolves, a sliding window technique is used to compute rhythmicity; values >0.6 indicate a high rhythmicity and high degree of dynamical coupling among the neurons generating those waves; values between 0.3 and 0.6 reflect moderate rhythmicity; and values <0.3 indicate low rhythmicity as seen in poorly organized seizures. High rhythmicity (absolute or relative to their pre-ictal value) appears to be predictive of a beneficial response to brain electrical stimulation (FIG. 37).

Since among several factors, the probability of seizure blockage using electrical currents seems dependent upon the degree of rhythmicity which varies during/within a seizure, the following strategy may prove useful to increase the likelihood of blockage: the degree of neuronal synchronization using a measure of rhythmicity or synchronization is tracked and, if its value during a seizure is above or below a level or value associated with low probability of seizure blockage or attenuation (value which may vary between seizures from the same site, between brain regions and subjects) this measure's value is first decreased (if it is above the value associated with high probability of a beneficial response) or increased (if below said value) by delivering appropriately timed monophasic, biphasic but not charge-balanced or charge-balanced pulses to a seizure, a step that is followed by re-delivery of electrical pulses timed to coincide with the decrease or increase in rhythmicity to within the values associated with high probability of seizure blockage or attenuation. Thermal, drug, chemical, or optical pulses may be delivered instead of or in addition to electrical ones.

Morphology/phase differences in response to electrical pulses are predictive of a positive (seizure blockage) or negative (no blockage) therapeutic outcome and thus useful as feedback for optimizing a therapy. Several methods exist to compare the shape of waves (without or with suitable transformations) including but not limited to root mean square error and variations of the Dynamic Time Warping such as Fast Dynamic Time Warping, Adaptive Feature Based Dynamic Time Warping, Dynamic Derivative Time Warping, Qualitative Approximation to Dynamic Time Warping. Other measures of distance (i.e., Euclidian, Manhattan, Chebyshev) may be used whenever applicable.

The probability of success in controlling undesirable events depends among other factors on: (a) the quality of spatio-temporal sampling of the signals which, in turn, is based on the type, geometry, and density of electrode arrays and the stability and quality of the electrode-tissue interface (U.S. Pat. No. 7,006,859, which is hereby incorporated herein by reference); (b) time and site of delivery of the therapy in relation to the known or predicted onset of undesirable changes; (c) parameter selection (frequency, intensity, waveform shape, etc.,) in the case of electrical stimulation, or drug type and dose in the case of pharmacological therapy) as a function of space-time dynamics of the pathological process; (d) phase/time of the circadian cycle, when the undesirable changes occur, their intensity, duration and extent of spread; and (e) time elapsed from previous events and their severity (defined as the average of their intensity), duration and extent of spread. The prior art does not investigate, in either real-time or off-line, and does not take into account these essential considerations that are necessary to optimize control of the undesirable events and prevent loss of function. Such considerations are particularly important for preventing or blocking paroxysmal events such as seizures, cardiac arrhythmias and pain whose behavior is shaped by the substrate in which they occur along with other factors, some of which are stochastic in nature.

Current methods or therapies for preventing, blocking or abating undesirable or abnormal state changes that rely on vehicles or media that must diffuse or travel through tissue (from the source(s) to the target(s) to perform their actions) do not adequately account for delays, uneven diffusion, and, in the case of oscillations/waves, the possibility of formation of intermediate frequencies (heterodyning) or aliasing which, in turn, may result in undesirable (or desirable) but uncontrollable resonances with the frequency at which the neurons or heart cells oscillate.

Delays in diffusion resulting in uneven charge densities in the case of currents, or of concentrations in the case of drugs/compounds, or of temperatures in the case of cooling, in reaching their target likely compromise efficacy and are not only the result of the degree of tissue anisotropy from where the state change takes place, but also of the size and macroscopic shape of the tissue. Size and macroscopic shape are important since the abnormal/undesirable activity also diffuses through tissue with (a) certain speed(s) and direction(s). Improvements provided by our work include: (a) monitoring and controlling, in real time and at the appropriate spatio-temporal scale, the space-time dynamics of a diffusive pathological process through optimization of the space-time dynamics of a diffusive therapy's (current densities, drug concentration or temperature) direction, speed and extent of diffusion and (b) using signals and scales representative of the space-time dynamics of the pathological process as feedback to optimize in real-time (and off-line for some applications) the space-time dynamics of the therapy.

This approach requires that the pathological events' signals or defining features be adequately sampled spatio-temporally, and that timing of delivery, spatial diffusion and other features of the therapy be adjusted/controlled as a function of local and global space-time dynamics including those of the tissue and its components such as neurons, heart cells, etc. Since both the abnormal events and the therapies are diffusive processes, spatio-temporal and geometric factors that cause differences in speed, direction, shape and distances between the advancing fronts of, for example, a seizure and those of the therapy, if not detected (or if detected but not timely corrected to avoid either undesirable resonances in the case of currents or inadequate charge density, drug concentrations or temperatures), are likely to lack efficacy or exert a paradoxical effect, enhancing the undesirable event.

Linear and non-linear, parametric and non-parametric, geometric/graphical, statistical and conventional and high order spectral methods exist for measuring, comparing and modeling brain activity that may be used in this invention. Also, brain activity may be recorded in multiple domains: electrical, magnetic, thermal, optical, chemical, acoustic, mechanical (e.g. pressure or movement) in any combination using commercially available sensors and analyzed using myriad available methods in the time or frequency domains. Models of: a) the abnormal activity (without treatment); b) the behavior of the therapy in a controllable virtual medium and c) of the interactions of the abnormal activity and the therapy will be built for optimization purposes.

The present invention is the first to take into account that therapy delivered to tissue is influenced by the space-time-state tissue dynamics and, in this sense, is a dependent (not an independent) variable to which tools and means for addressing the inherent but manageable limitations may be applied to adapt and optimize the therapy as needed not only for each subject, but also for the region from where the undesirable brain activity originates, the state of the system (e.g. awake vs. asleep) or time of day. The cytoarchitectonic diversity of the cortical mantle and of subcortical structures must be factored into the strategies for therapy delivery. Location, type, size and number of sensors for signal analyses and of therapy sources and type(s), are of paramount importance for prevention, blockage or abatement of seizures, cardiac arrhythmias or pain. The inventive system disclosed herein has the ability to track/measure tissue resistivity, osmolality and tissue responses, among other variables, and use latencies, amplitudes, waveforms/types and actual frequencies and periods of the responses to create maps as a function of time and state that are used to adjust automatically or manually, therapies to improve safety, efficacy, and tolerability. Measurements of resistivity, osmolality, diffusivity, temperature, ionic and neurotransmitter concentrations, pressure/strain, motility, acoustic activity and of responses to electrical, chemical, physiological (e.g., visual), cognitive and affective stimulation may be performed with commercially available sensors. Specific mention is made of measuring cognitive functions, the most meaningful index of therapeutic efficacy (especially in the case of partial complex or generalized seizures) and of using these measures to adapt and optimize therapies.

The present invention overcomes the limitations of the prior art by: (a) quantifying and characterizing in real-time and, when advantageous off-line, the electrical, chemical, thermal, mechanical, acoustic and cognitive (for brain) behavior of biological tissues at one or more spatial scales using passive and active probes; (b) recording with precision and high fidelity not only the conventional frequencies (0.1-100 Hz) but also ultra-slow (e.g., 0.001 Hz) and ultra-fast (>500 Hz) oscillations; (c) using this information to determine (and adapt and update as needed) the type of therapy, timing of delivery, location, geometry and number of therapy sources, duration and frequency/rate of therapy delivery, the top priority being to prevent the event from occurring, the second one to block the event before the subject is impaired, and the third one to lessen severity if blockage is not feasible, so as to minimize dysfunction, delivering a warning if prevention fails and logging to memory all relevant data about the spatio-temporal behavior of the brain activity and of the therapy.

Sensors of the present invention may be multimodal (e.g., electrical, optical, chemical, pressure, thermal, acoustic, etc.). Their number location, functions, and status (active or dormant) may vary according to the task at hand. Similarly, therapy sources of the present invention may be multimodal (e.g., electrical, magnetic, chemical, thermal, mechanical, etc). Their number locations and functions, and status (active or dormant) may vary according to the task at hand.

In one embodiment, assessment of the spatio-temporal effects of therapy are performed in one or more dimensions, at one or more sites and at one or more points in time and time-scales according to the following steps listed in their order of execution: 1. Determine the spatio-temporal behavior of a seizure and of a therapy response on-line or off-line, using the tissue electrical oscillations to estimate: a) power at one or more frequencies; b) waveform or rhythmicity values of said oscillations; c) rate of spread or diffusion the abnormal and therapeutic electrical activity; d) extent of spread and the geometry or shape of the advancing abnormal and therapeutic electrical oscillations graphed, for example, as contour plots (see FIG. 35); e) changes in power at one or more frequencies; f) rate of change in power; g) changes in rhythmicity values at one or more frequencies at one more sites, at one or more times; h) rate of change in rhythmicity values at one or more frequencies; 2. Build probability density (or probability distribution) functions using one or more values or their suitable mathematical transformation of each of the seizure signal and of the therapy response features listed immediately above and create a library of catalogued events (seizures in this embodiment) and of treatment modalities and parameters; 3. Estimate in which interval (if at all) of the probability density function the values of the observed event and of therapy response fall; 4. Based on where in the probability density function the seizure or the response therapy) values fall, estimate the probability with which: a) the seizure matches a known seizure type from a certain site in a certain subject and b) the therapy response is beneficial or detrimental (for simplicity, modalities or treatment parameters without any effect on seizures are classified as detrimental); 5. If the seizure does not match with good probability a known type, said seizure is saved into a library of unmatched events; if the therapy response is beneficial or detrimental, the modality and parameters used are saved to their respective libraries; 6. If the therapy response is adverse, a modality or parameter optimization search is launched and the results of each attempts are logged and saved to either the beneficial or detrimental library and used to narrow the search space (FIGS. 38, 39). Existing search and optimization theory and methods will be applied on-line or off-line in an automated and iterative manner using the feature values of the seizure and of the therapy response as cost functions.

In other embodiments, other signals including but not limited to magnetic, thermal, chemical or optical and their suitable features (e.g. concentrations of an ion in the case of chemical signals) or their mathematical transformations may be used to build the statistical distributions and libraries of seizure features or properties (in one or more dimensions, at one or more sites and at one or more times and time scales. The methods and processes described for electrical therapies apply to thermal, pharmacologic and other therapy modalities.

The values of seizure properties or features and their spatio-temporal behavior obtained without treatment are considered control values against which those obtained with treatment will be compared. These values may be ranked according to their magnitude and stratified according to site of origin, type and time of day, wake-sleep cycle, and cognitive state (relaxed awake or attentive awake) among others for logging (with appropriate time stamping) and saving in the event library. The same procedure will be applied to the values of features obtained during the seizure-therapy interactions and the ensuing response.

Maps and other graphical means for plotting and displaying the spatiotemporal behavior of feature values of the seizures and of the therapy response may be also used and logged and saved into libraries for comparison purposes. Said comparison may be performed using shape similarity measures such as shape context, Hausdorff contour, Distance set correspondence, Dice and cosine coefficients (in the case of numerical feature vectors) among many other available methods. Shape descriptors such as D2 shape distributions, extended Gaussian maps, Gaussian Euclidian distance transforms may be also used for this purpose. Shape matching, for comparing the shapes of seizure maps or of therapy response maps, may be performed using the wavelet transform modulus maxima, among other techniques known to the person of ordinary skill in the art.

For electrical therapy (such as that described in U.S. Pat. No. 6,934,580, hereby incorporated herein by reference), the following approaches may be pursued:

(a) generate direct and alternating currents, either simultaneously or sequentially in a predetermined pattern;

(b) deliver currents to multiple sites at the same or different intensities possibly including a different intensity for the cathode as opposed to the corresponding anode wherein all anodes may have identical or differing intensities wherein alternating currents can be delivered without being fully charge-balanced, even though each phase for a given intensity is balanced;

(c) deliver the currents to multiple sites at the same or different frequencies;

(d) deliver the currents to multiple sites using the same or different pulse widths;

(e) deliver the currents to multiple sites using the same or different waveforms;

(f) deliver the currents to multiple sites using the same, different, or varying polarities;

(g) deliver alternating currents to multiple sites using the same, fully or incompletely charge-balanced pulses;

(h) change the number and/or geometric configuration or arrangements of the contacts to which current is delivered;

(i) deliver amplitude modulated currents to multiple sites using suitable carriers to thereby increase signal/noise ratios and enhance tissue penetration;

(j) deliver frequency modulated currents to multiple sites using suitable carriers to thereby increase signal/noise ratios and enhance tissue penetration;

(k) multiplex delivery of currents from their sources to take into account (i) differences in speed of diffusion (particularly of its front) of the pathological process, and also (ii) distances between the site of origin of pathologic process and therapy sources;

(l) change the orientation/direction, field size and strength of the therapy;

(m) deliver fractal electrical waves;

(n) use multiple electrodes or therapy sources at single or multiple sites.

The concept of simultaneously delivering current at different intensities, is equally applicable to frequencies, pulse widths and waveforms. As an example of another application, electrodes may be arranged in a circle with a plurality of anodes encircling a single, centrally located cathode. For direct current applications, the polarities may be changed for each pair of electrodes.

Other strategies by which therapies may be optimized include but are not limited to:

1. Modification (augmentation or reduction) of their rate, direction, concentration, density of flow or diffusivity, and type of drug(s) or electrical pulse(s) used.

2. Simultaneous or consecutive use of more than one therapeutic modality (e.g, electrical and thermal therapies, electrical and pharmacological therapies, etc.).

Means by which diffusivity, direction, concentration, or density of a therapeutic medium may be modified include, but are not limited to:

1. Increasing or decreasing (a) tissue pressure using physical or chemical agents (e.g., manitol infusion to a certain region); (b) increasing or decreasing tissue temperature to create "sinks" or "barriers" to diffusion or to facilitate diffusion.

2. Changing the degree of lypophilicity or hydrophilicity of compounds or changing surface tension of the extracellular space, or increasing or decreasing the tortuosity (using mechanical or chemical means) of the extracellular space through which diffusion of ions, neurotransmitters, and other compounds takes place.

3. Releasing inactive compounds well in advance of events so as to allow them to reach the target in sufficient concentration and activate them in response to the prediction or detection of an event such as a seizure. This may be accomplished for instance, via viral transfection and implantation of fiberoptic fibers in the target area.

4. Increase the number of therapy source without causing undesirable tissue disruption through the use of micro- or nanodevices, or changing their location or orientation.

Some applications of the present invention may include logging to memory the outcomes of therapy as a function of local space-time-state dynamics, and applying, on-line or off-line, existing search and optimization methods in an automated and iterative manner, and using cost functions, such as event severity or type of adverse event cause by the therapy.

Spatio-temporal characterization of nervous activity (electrical, magnetic, thermal, chemical, acoustic, kinetic, pressure/load/strain, cognitive) may be performed using existing state-of-the-art linear or non-linear, parametric or non-parametric uni- or multi-dimensional signal processing and analyses methods (See also U.S. Pat. Nos. 5,995,868; 6,549,804; 6,768,969; 6,793,670; 6,934,580; 6,904,390; 7,054,792; 7,188,053). Therapeutic modality and parameter search for optimization of efficacy may be performed using methods such as simulated annealing, search, and genetic algorithms.

FIGS. 38-39 provide details about the process of therapy optimization, applicable to any therapeutic modality (pharmacological, thermal, electrical, ablative) and to any medical disorder.

All the approaches, methods and strategies described above may be used to optimize the therapy by decreasing the frequency, intensity, duration of adverse events or by minimizing the probability of occurrence of the most serious, disabling or intolerable adverse effects, without necessarily increasing the efficacy of the therapy.

In one embodiment, the present invention provides a method for assessment, optimization and logging of the effects of a therapy for a medical condition. In one embodiment, the method comprises:

(a) receiving into a signal processor input signals indicative of the subject's brain activity;

(b) characterizing the spatio-temporal behavior of the brain activity using the signals;

(c) delivering a therapy to a target tissue of the subject;

(d) characterizing the spatio-temporal effect of the therapy on the brain activity;

(e) in response to the characterizing, optimizing at least one parameter of the therapy if the brain activity has not been satisfactorily modified or has been adversely modified by the therapy;

(f) characterizing the spatio-temporal effect of the at least one optimized parameter; and (g) logging to memory the at least one optimized parameter.

In one embodiment, the method further comprises logging to memory at least one effect of the optimized therapy on the subject's brain activity.

In one embodiment, step (d) comprises quantitatively characterizing the spatio-temporal effect of the therapy on the brain activity. Alternatively or in addition, in one embodiment, step (d) comprises semi-quantitatively or qualitatively characterizing the spatio-temporal effect of the therapy on the brain activity.

A variety of medical conditions may be considered. In one embodiment, the medical condition is epilepsy.

Various steps of the method can be performed at various times. In one embodiment, steps (a) through (e) are performed at or before one or more of the electrographic onset of a seizure, the clinical onset of a seizure, a loss of responsiveness, a loss of consciousness, the electrographic termination of a seizure, a recovery of consciousness, or a recovery of responsiveness.

Any appropriate input signals may be used. In one embodiment, the input signals are one or more of electrical signals, magnetic signals, thermal signals, optical signals, chemical signals, or cognitive signals.

In a further embodiment, when the input signals are electrical signals, characterizing the spatio-temporal behavior is performed in real-time using time-frequency-energy information in one, or more dimensions, at one or more time scales;

when the input signals are magnetic signals, characterizing the spatio-temporal behavior is performed in real-time using time-frequency-energy information in one or more dimensions and at one or more time scales;

when the input signals are thermal signals, characterizing the spatio-temporal behavior is performed in real-time using time-frequency-energy information in one or more dimensions and at one or more time scales;

when the input signals are optical signals, characterizing the spatio-temporal behavior is performed in real-time using time-frequency-energy information in one or more dimensions and at one or more time-scales;

when the input signals are chemical signals, characterizing the spatio-temporal behavior is performed in real-time by measuring their concentrations and rate of diffusion through the extracellular space, rate of re-uptake into synapses or glia in one or more dimensions and at one or more time scales; or when the input signals are cognitive signals, the input signals relate to at least one of reaction time, attention, verbal, non-verbal or procedural short-term memory, verbal, non-verbal or procedural long-term memory, language fluency or comprehension, visuo-spatial functions, auditory discrimination, visual discrimination, abstract reasoning, calculation, and judgment.

Any appropriate therapy for the medical condition may be considered. In one embodiment, which may be appropriate when the medical condition is epilepsy, the therapy comprises one or more of an electrical therapy, a magnetic therapy, a chemical therapy, a heating therapy, a cooling therapy, applying a pressure to a target tissue, applying a vacuum to a target tissue, an optical therapy, a cognitive therapy, a sensory therapy, or a motor therapy.

The therapy may be administered at any appropriate time, depending on the medical condition, the therapy, and other factors apparent to the person of ordinary skill in the art having the benefit of the present disclosure. In one embodiment, delivery of the therapy is based on degradation of one or more cognitive signals. In a further embodiment, the cognitive signal is a level of responsiveness.

In one embodiment, optimizing comprises at least one of changing the target tissue, adding at least one therapy element, and changing a different type of therapy element.

The present invention also provides a method for optimizing the effect of a therapy. In one embodiment, the method comprises determining a wave rhythmicity of brain activity of a subject, and applying a therapy to a target tissue of the subject at a first time, wherein the target tissue and the first time are based upon the wave rhythmicity.

The present invention also provides a method for optimizing the effect of a therapy. In one embodiment, the method comprises estimating the level of synchrony within one brain epileptogenic region, and determining if the level of synchrony is above or below a value associated with a high probability of blockage of an epileptic event when the therapy is applied. In a further embodiment, delivery of the therapy is timed to coincide with the synchrony level reaching the value associated with the high probability of blockage of the epileptic event.

In one embodiment, the present invention provides a method of optimizing the effects of a therapy. In one embodiment, the method comprises:

(a) determining the spatio-temporal behavior of one or more of a patient's seizures and the patient's response to a therapy in one or more dimensions, at one or more sites, at one or more points in time, at one or more time-scales, and at one or more frequencies;

(b) building a probability density function based on the spatio-temporal behavior;

(c) creating a library of seizure features;

(d) cataloging the one or more seizures according to a degree of similarity to at least one of the seizure or therapy response features;

(e) classifying the one or more seizures as known or unknown;

(f) creating a library of treatment and parameter modalities;

(g) classifying the treatment modalities as beneficial or detrimental;

(h) saving at least one feature of the one or more seizures into a library of unmatched events if it does not match a known seizure type;

(i) saving at least one therapy response to a beneficial treatment library if it is beneficial or to a detrimental treatment library if it is detrimental;

(j) optimizing the therapy parameters; and (k) saving the optimized parameters.

Any one or more of the above steps may be performed on-line or off-line.

In one embodiment, determining the spatio-temporal behavior comprises at least one of estimation of power and its rate of change, estimation of one or more rhythmicity values and their rate of change, or estimation of the extent, rate of spread and shape of spread of abnormal and therapeutic electrical activities.

In one embodiment, classifying the one or more seizures comprises estimating an interval of the probability density function into which the values of the one or more seizures fall and classify the seizure as known or unknown based on the interval.

In one embodiment, classifying the treatment modalities comprises estimating the interval of the probability density function in which one or more of the seizure or the response therapy fall, and using the estimate to determine the probability with which the seizure matches a known seizure type from the site in the patient and the probability that the therapy response is beneficial or detrimental.

In one embodiment, the present invention provides a method for quantitative assessment, optimization and logging of the effects of a therapy for a medical condition. The method comprises:

(a) receiving into a signal processor input signals indicative of the subject's brain activity and characterizing the spatio-temporal behavior of the brain activity using the signals (c) delivering a therapy to a target tissue of the subject;

(d) characterizing the spatio-temporal effect of the therapy on the subject's brain activity;

(e) in response to the characterizing, optimizing the therapy if the subject's brain activity has not been satisfactorily modified by the therapy;

(f) characterizing the spatio-temporal effects of the parameters; and (g) logging to memory the optimized therapy parameters.

In one embodiment, the method further comprises logging to memory at least one effect of the optimized therapy on the subject's brain activity.

In one embodiment, the method further comprises performing steps (a) through (f) at or before the onset of a brain activity of interest.

In one embodiment, steps (a) through (e) are performed before a transition into a seizure state is complete.

In another embodiment, steps (a) through (e) are performed at or after the electrographic onset of a seizure but before the first clinical manifestation (i.e. before clinical onset).

In another embodiment, steps (a) through (e) are performed at or after clinical onset but before a loss of responsiveness.

In another embodiment, steps (a) through (e) are performed at or after a loss of responsiveness but before a loss of consciousness.

In another embodiment, steps (a) through (e) are performed at or after a loss of consciousness but before the termination of electrographic activity.

In another embodiment, steps (a) through (e) are performed at or after the termination of electrographic activity but before a recovery of consciousness or before a recovery of responsiveness.

In another embodiment, steps (a) through (e) are performed at or after a recovery of responsiveness.

One or more of the various steps can be performed in real-time (i.e., substantially without delay) or not in real-time. Alternatively or in addition, one or more of the various steps can be performed by a first device in proximity to or implanted into the body of the subject, or by a second device capable of being in communication with a first device. The second device may be continually in communication with the first device, or may sporadically be in communication with the first device, such as only when uploading data from or downloading data to the first device. Performance of one or more of steps (a) through (e) by a second device in the latter scenario may be referred to as "off-line" performance. In one embodiment, steps (a) through (e) are performed off-line.

The subject may have any medical condition of interest and/or any other physiological activity of interest. In one embodiment, the subject's brain activity of interest is an epileptic seizure.

In one embodiment, the input signals are electrical signals and the spatio-temporal behavior is characterized in real-time using time-frequency-energy information in one, or more dimensions, at one or more time scales.

In a further embodiment, characterizing the spatio-temporal behavior of the brain activity comprises quantifying at least one of power at different frequencies, the extent and shape of the spatial extent of the electrical signals, and the direction and rate of spread of the electrical signals.

In one embodiment, the input signals are magnetic signals and the spatio-temporal behavior is characterized in real-time using time-frequency-energy information in one or more dimensions and at one or more time scales.

In a further embodiment, characterizing the spatio-temporal behavior of the brain activity comprises quantifying at least one of power at different frequencies, the extent and shape of the spatial extent of the magnetic signals, and the direction and rate of spread of the magnetic signals.

In one embodiment, the input signals are thermal signals and the spatio-temporal behavior is characterized in real-time using time-frequency-energy information in one or more dimensions and at one or more time scales. Though not to be bound by theory, doing so may allow the operator of the method to quantify their space-time dynamics.

In one embodiment, the input signals are optical signals and the spatio-temporal behavior is characterized in real-time using time-frequency-energy information in one or more dimensions and at one or more time-scales. Though not to be bound by theory, doing so may allow the operator of the method to quantify their space-time dynamics.

In one embodiment, the input signals are chemical signals and the spatio-temporal behavior is characterized in real-time by measuring their concentrations and rate of diffusion through the extracellular space, rate of re-uptake into synapses or glia in one or more dimensions and at one or more time scales. Though not to be bound by theory, doing so may allow the operator of the method to quantify their space-time dynamics.

In one embodiment, the spatio-temporal effects characterized include at least one of the power at different frequencies, wave morphology, rate, direction, density, spatial extent and shape of diffusion of the therapy in the tissue.

In a further embodiment, characterizing the spatio-temporal behavior of the brain activity comprises mapping the brain activity in one or more dimensions at one or more time scales, and characterizing the spatio-temporal effect of the therapy comprises mapping the effects in one or more dimensions and at one or more temporal scales, the method further comprising comparing the brain activity map and the spatio-temporal therapy effects map.

In one embodiment, optimizing the therapy comprises optimizing at least one of the site, rate of delivery, direction, density, and spatial extent of the therapy based upon the comparing the brain activity map and the spatio-temporal therapy effects maps.

In a further embodiment, a brain activity of interest is an epileptic seizure, and wherein mapping the brain activity and mapping the therapy effects are performed at a time when a seizure is not occurring.

In another further embodiment, mapping the brain activity and mapping the effects are performed as a function of at least one of sleep-wake state, circadian rhythms, and spatio-temporal dynamics history.

In one embodiment, optimizing comprises at least one of changing a target tissue, adding at least one therapy element, and adding a different type of therapy element.

In one embodiment, optimizing comprises at least one of changing the target tissue, adding at least one therapy element, and changing a different type of therapy element.

In one embodiment, characterizing the spatio-temporal behavior of the brain activity comprises performing at least one laminar field analysis.

In one embodiment fractal or multi-fractal analysis is performed to characterize the space-time dynamics of the abnormal activity and of the spatio-temporal therapy effects.

The signals can be collected, recorded, and stored using any appropriate technique, as a matter of routine experimentation to the person of ordinary skill in the art having the benefit of the present disclosure. In one embodiment, the signals are recorded between 0 (DC) and 10 KHz. In another embodiment, the signals are sampled at more than one frequency and with more than one degree of precision.

Any therapy can be delivered to any target tissue of the subject. In one embodiment, the delivered therapy comprises one or more of an electrical therapy, a magnetic therapy, a chemical therapy, a heating therapy, a cooling therapy, applying a pressure to a target tissue, applying a vacuum to a target tissue, an optical therapy, a cognitive therapy, a sensory therapy, and a motor therapy.

In one embodiment, therapy delivery is based on a degradation of cognitive signals. In a further embodiment, the cognitive signal is a level of responsiveness, such as may be determined from a complex time reaction test.

In one embodiment, therapy optimization is based on a measurement of cognitive signals. In a further embodiment, the cognitive signal upon which therapy optimization is based is a level of responsiveness.

In one embodiment, the present invention also provides a method for optimizing the effect of a medical therapy. In one embodiment, the method comprises determining wave rhythmicity and applying a therapy to a target tissue at a first time, wherein the target tissue and the first time are based upon the wave rhythmicity.

In one embodiment, the present invention also provides a method for optimizing the effect of a therapy. In one embodiment, the method comprises estimating the level of synchrony within one brain epileptogenic region, and determining if it is above or below a value associated with high probability of blockage when a therapy is applied. In a further embodiment, delivery of electrical, thermal or drug pulses is timed to coincide with the synchrony level reaching a value associated with high probability of therapeutic efficacy.

In one embodiment, the present invention also provides a method for quantitative assessment, optimization, and logging of the adverse effects of a therapy for a medical condition. In one embodiment, the method comprises:

(a) receiving into a signal processor input signals indicative of the subject's brain activity and characterizing the spatio-temporal behavior of the brain activity using the signals;

(b) characterizing the spatio-temporal effect of the therapy on the subject's brain activity;

(c) determining if the therapy causes adverse events;

(d) characterizing quantitatively, semi-quantitatively or qualitatively the type, frequency, intensity and duration of the adverse effect;

(e) modifying the therapy to decrease the frequency, intensity, duration, or type of adverse effect; and (f) logging to memory the optimized effects of the therapy on the subject's brain activity.

In one embodiment, the present invention also provides a method for quantitative assessment, optimization and logging of the adverse effects of a therapy for a medical condition. In one embodiment, the method comprises:

(a) receiving into a signal processor input signals indicative of the subject's brain activity and characterizing the spatio-temporal behavior of the brain activity using the signals;

(b) characterizing the spatio-temporal effect of the therapy on the subject's brain activity;

(c) determining if the therapy causes adverse events;

(d) characterizing quantitatively the type, frequency, intensity and duration of the adverse effect;

(e) modifying the therapy to decrease the frequency, intensity, duration, or type of adverse effect; and (f) logging to memory the optimized effects of the therapy on the subject's brain activity.

In one embodiment, the present invention also provides a method for semi-quantitative or qualitative assessment, optimization and logging of the adverse effects of a therapy for a medical condition. In one embodiment, the method comprises:

(a) receiving into a signal processor input signals indicative of the subject's brain activity and characterizing the spatio-temporal behavior of the brain activity using the signals;

(b) characterizing the spatio-temporal effect of the therapy on the subject's brain activity;

(c) determining if the therapy causes adverse events;

(d) characterizing semi-quantitatively or qualitatively the type, frequency, intensity and duration of the adverse effect;

(e) modifying the therapy to decrease the frequency, intensity, duration, or type of adverse effect; and (f) logging to memory the optimized effects of the therapy on the subject's brain activity.

FIGS. 38-39 shows a flowchart depiction of one method, in accordance with the present invention. Turning to FIG. 38, a signal is acquired and processed 105, and analyzed 110. Based on the analysis 110, an event is detected 115.

If no event is detected 115, flow returns to signal acquiring and processing 105. If an event is detected 115, a multi-feature characterization 120 is performed. Based on the multi-feature characterization 120, it is determined 125 if the event matches an entry in an event library.

If the event does not match, the event is saved 130 in a library of unmatched events. A treatment library is then searched 135 for a treatment modality and parameters that may be efficacious in treating the event. A treatment is performed (not shown), and it is determined 140 whether the treatment modality and parameters are efficacious. If they are efficacious, this information is saved 145 in the treatment library. If not, flow returns to the search 135.

FIG. 39 shows a matched event analysis 200 taking place if the event matches an entry in an event library in determination 125. A treatment library is searched 235 for a treatment modality and parameters that may be efficacious in treating the event. A treatment is delivered 237, and it is determined 240 whether the treatment modality and parameters are efficacious. If they are efficacious, flow returns to signal acquiring and processing 105.

If they are not efficacious, they are saved 245 in a nonefficacious treatment library. A multi-feature characterization 250 is performed. Based on the multi-feature characterization 250, it is determined 255 if the event is of a new type, meaning one that does not match an entry in the event library.

If the event is a new type according to determination 255, it is saved 230 in a library of unmatched events, and flow returns to the search 135.

If the event is not a new type according to determination 255, it is determined 260 if the treatment modality and parameters are accurately matched to the event type. If not, the treatment modality and parameters are changed, i.e., the error is corrected 265. However, if they are accurately matched to the event type, they are retested 270. If the retested treatment modality and parameters are found 275 to be efficacious, this information is saved 280 in the treatment library. If not, flow returns to the search 135.

Any method discussed herein may be performed by a computer readable program storage unit encoded with instructions that, when executed by a computer, perform the method.

All of the methods and apparatuses disclosed and claimed herein may be made and executed without undue experimentation in light of the present disclosure. While the methods and apparatus of this invention have been described in terms of particular embodiments, it will be apparent to those skilled in the art that variations may be applied to the methods and apparatus and in the steps, or in the sequence of steps, of the method described herein without departing from the concept, spirit, and scope of the invention, as defined by the appended claims. It should be especially apparent that the principles of the invention may be applied to selected cranial nerves other than, or in addition to, the vagus nerve to achieve particular results in treating patients having epilepsy, depression, or other medical conditions.

Appendix: Cortex Morphometrics and electrical properties Human cortical thickness: mean: ~2.5 mm (range: 1.45-4.5 mm). Approximately 80% of cortical neurons are pyramidal. The intracellular space is in the order of 100-200 A. Thalamic afferents to the cortex are grouped in bundles or columns with a diameter of 100-500-um. Cortical columns have a diameter of 200-500 nm. Cortical macrocolumns (diameter ~0.5-3 mm; height ~2.5 mm) lies near the apparent theoretical limit of spatial resolution available in scalp recordings. This macrocolumns apparently constitutes a distinct unit of neocortical dynamic function. Simultaneous interactions can also be expected to take place at other spatial scales (for example between neurons, minicolumns, corticocortical columns, cytoarchitectonic regions and so on. A cortical macrocolumn contains $10^5$-$10^6$ neurons and $10^{10}$ synapses. The distance to which cells in the macrocolumn send collaterals (~3 mm) provides one definition of their spatial scale. Minicolumns (diameter ~20-50 um) also has been proposed as a basic functional unit of neocortex; these can be defined by the characteristic lateral spread of axons of inhibitory neurons. A minicolumn spanning the entire cortical thickness contains ~110 neurons lined up along its axis (striate cortex contains ~260 neurons)

Brodmann's identified two types of cortices in the human brain:

a) Homogenetic: Has 6 layers. It is also know as neocortex, isocortex, neopallium or supralimbic;

b) Heterogenetic: <6 layers. It is also known as allocortex. There are 2 types of heterogenetic cortex: archipallium (hippocampus, dentate gyms and subiculum) and paleopallium (pyriform area). The transition between heterogenetic and homogenetic is known as mesocortex.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed:

1. A medical device configured to treat an epileptic event comprising:
    one or more processors configured to determine a wave rhythmicity of brain activity of a patient, and
    a treatment unit configured to apply a therapy to a target tissue where the target tissue is based upon the wave rhythmicity of the patient at a first time where the first time is based upon the wave rhythmicity.

2. The medical device of claim 1, wherein the therapy includes at least one of an electrical treatment, a thermal treatment, a drug treatment, and a chemical treatment.

3. The medical device of claim 2, wherein the electrical treatment includes at least one of: delivering direct currents;

delivering alternating currents; delivering currents to multiple sites at one or more intensities; delivering currents to multiple sites at one or more frequencies; delivering currents to multiple sites at one or more pulse widths; delivering currents to multiple sites at one or more waveforms; and delivering currents to multiple sites using one or more polarities.

4. The medical device of claim 1, wherein the one or more processors are configured to determine a second therapy based on patient specific data, where the second therapy is tailored to the patient based on the patient specific data.

5. The medical device of claim 4, wherein the treatment unit is further configured to deliver the second therapy to the patient.

6. The medical device of claim 4, wherein at least one of: a time of therapy delivery; a therapy intensity; a therapy dosage; a type of therapy; a therapy delivery location; a geometric configuration; and a number of therapy sources are part of the tailoring procedure.

7. The medical device of claim 1, wherein the one or more processors are further configured to determine a therapy effect on a brain activity and modify the therapy based on the determined therapy effect on the brain activity.

8. The medical device of claim 1, wherein the therapy has low efficacy based on a low rhythmicity.

9. The medical device of claim 8, wherein the one or more processors are configured to initiate a second therapy based on the low rhythmicity.

10. The medical device of claim 1, wherein the one or more processors are configured to generate a warning based on the wave rhythmicity.

\* \* \* \* \*